United States Patent [19]
Bujard et al.

[11] Patent Number: 5,654,168
[45] Date of Patent: Aug. 5, 1997

[54] TETRACYCLINE-INDUCIBLE TRANSCRIPTIONAL ACTIVATOR AND TETRACYCLINE-REGULATED TRANSCRIPTION UNITS

[75] Inventors: Hermann Bujard, Heidelberg, Germany; Manfred Gossen, Berkeley, Calif.

[73] Assignees: BASF Aktiengesellschaft; Knoll Aktiengesellschaft, both of Ludwigshafen, Germany

[21] Appl. No.: 275,876

[22] Filed: Jul. 15, 1994

Related U.S. Application Data

[63] Continuation-in-part of Ser. No. 270,637, Jul. 1, 1994, abandoned.
[51] Int. Cl.⁶ .................. C12P 21/00; C12N 15/00; C12N 15/63; C07H 21/04
[52] U.S. Cl. ............... 435/69.1; 435/172.3; 435/320.1; 536/23.7; 536/24.1
[58] Field of Search ................... 435/69.1, 172.3, 435/320.1; 536/23.7, 24.1

[56] References Cited

U.S. PATENT DOCUMENTS

| | | | |
|---|---|---|---|
| 4,833,080 | 5/1989 | Brent et al. | 435/172.3 |
| 5,221,778 | 6/1993 | Byrne et al. | 800/2 |

FOREIGN PATENT DOCUMENTS

| | | |
|---|---|---|
| 0 332 416 | 9/1989 | European Pat. Off. . |
| 0 455 424 A3 | 11/1991 | European Pat. Off. . |
| 0 455 687 B1 | 11/1991 | European Pat. Off. . |
| 0 494 724 A2 | 7/1992 | European Pat. Off. . |
| WO91/19784 | 12/1991 | WIPO . |
| WO91/19796 | 12/1991 | WIPO . |
| WO92/11874 | 7/1992 | WIPO . |
| WO92/20808 | 11/1992 | WIPO . |
| WO93/04169 | 3/1993 | WIPO . |
| WO93/23431 | 11/1993 | WIPO . |
| WO94/04672 | 3/1994 | WIPO . |
| WO94/18317 | 8/1994 | WIPO . |
| WO94/29442 | 12/1994 | WIPO . |

OTHER PUBLICATIONS

Gossen, M., "Prokaryontische Repressor/Operatorsysteme in der Kontrolle der eukaryotischen Genexpression" (Inaugural–Dissertation, Universität Heidelberg), 1993.

Wissmann et al. Selection ofr Tn10 Tet repressor binding to tet operator in *Escherichis coli:* Isolation of temperature-–sensitive mutants and combinatorial mutagenesis in the DNA binding motif Genetics vol. 128 225–232 1991.

Mendez et al. Heterogeneity of tetracycline resistance determinants Plasmid vol. 3 99–108 1980.

Cowell, "Repression versus activation in the control of gene transcription," *Trends in Biochemical Sciences*, 19:1, 38–42 (1994).

Deuschle et al., "Tetracycline–reversible silencing of eukaryotic promoters," *Mol. Cell. Biol.*, 15:4, 1907–1914 (1995).

Gatz et al., "Stringent repression and homogeneous de–repression by tetracycline of a modified CaMV 35S promoter in intact transgenic tobacco plants," *The Plant Journal*, 2:3, 397–404 (1992).

Gossen et al., "Exploiting prokaryotic elements for the control of gene activity in higher eukaryotics," Keystone Symposium on Gene Therapy and Molecular Medicine, Steamboat Springs, Colorado, *Journal of Cellular Biochemistry*, Supplement 0 (21A), Abstract No. C6–220, 355 (1995).

Gossen et al., "Transcriptional activation by tetracyclines in mammalian cells," *Science*, 268:5218, 1766–1769 (1995).

Liang et al., "Enhanced and switchable expression systems for gene–transfer," Keystone Symposium on Gene Therapy and Molecular Medicine, Steamboat Springs, Colorado, *Journal of Cellular Biochemistry*, Supplement 0 (21A), Abstract No. C6–220, 379 (1995).

Brent, R. and M. Ptashne (1984) "A Bacterial Repressor Protein or a Yeast Transcriptional Terminator Can Block Upstream Activation of A Yeast Gene" *Nature* 312:612–615.

Brent R. and M. Ptashne (1985) "A Eukaryotic Transcriptional Activator Bearing the DNA Specificity of a Prokaryotic Repressor" Cell 43:729–736.

Hinrichs, W., et al., (1994) "Structure of the Tet Repressor–Tetracycline Complex and Regulation of Antibiotic Resistance", *Science*, vol. 264, pp. 418–420.

(List continued on next page.)

*Primary Examiner*—George C. Elliott
*Assistant Examiner*—John S. Brusca
*Attorney, Agent, or Firm*—Lahive & Cockfield; Giulio A. DeConti, Jr.

[57] ABSTRACT

Nucleic acid molecules and proteins useful for regulating the expression of genes in eukaryotic cells and organisms in an inducible manner are disclosed. In the regulatory system of the invention, transcription of a tet operator-linked nucleotide sequence is stimulated by a transcriptional activator fusion protein composed of two polypeptides, a first polypeptide which binds to tet operator sequences in the presence of tetracycline or a tetracycline analogue and a second polypeptide which directly or indirectly activates transcription in eukaryotic cells. In one embodiment, the fusion protein comprises a mutated Tet repressor operatively linked to a transcriptional activation polypeptide, such as a portion of herpes simplex virus virion protein 16. In the absence of an inducing agent (tetracycline or a tetracycline analogue), transcription of the tet operator-linked nucleotide sequence remains uninduced. In the presence of the inducing agent, transcription of the tet operator-linked nucleotide sequence is stimulated by the transactivator fusion protein of the invention. Novel transcription units which allow for coordinate or independent tetracycline-regulated expression of two or more nucleotide sequences by the transactivator fusion protein of the invention are also disclosed. Kits including the components of the regulatory system of the invention are also encompassed by the invention.

33 Claims, 10 Drawing Sheets

OTHER PUBLICATIONS

Hecht, B., et al., (1993) "Noninducible Tet Repressor Mutations Map from the Operator Motif to the C Terminus", *Journal of Bacteriology*, vol. 175, No. 4.

Gossen, M., et al., (1993) "Control of gene activity in higher eukaryotic cells by prokaryotic regulatory elements", *TIBS*, vol. 18, No. 12, pp. 471–475.

Fieck, A., et al., (1992) "Modification of the *E. coli* Lac Repressor for Expression in Eukaryoitic Cells: Effect of Nuclear Signal Sequence on Protein Activity and Nuclear Documentation", *Nucleic Acid Research*, vol. 20, pp. 1785–1791.

Seipel, K., et al., (1992) "Different activation domains stimulate transcription from remote ('enhancer') and proximal ('promoter') positions", *The EMBO Journal*, vol. 11, No. 13, pp. 4961–4968.

Epstein-Baak, R., et al., (1992) "Inducible Transformation of Cells from Transgenic Mice Expressing SV40 under Lac Operon Control", *Cell Growth & Differentiation*, vol. 3, pp. 127–134.

Gossen, M., and Bujard, H., (1992) "Tight control of gene expression in mammalian cells by tetracycline–responsive promoters", *Proceedings of the National Academy of Science* vol. 89, pp. 5547–5551.

Bradley, A., (1991) "Modifying the mammalian genome by gene targeting", *Current Opinion in Biotechnology*, vol. 2, pp. 832–829.

Wyborski, D.L., and Short, J.M., (1991) "Analysis of Inducers of the *E. coli* Lac Repressor System in Mammalian Cells and Whole Animals", *Nucleic Acid Research*, vol. 19, pp. 4647–4653.

Degenkolb, J., et al., (1991) "Structural Requirements of Tetracycline–Tet Repressor Interaction: Determination of Equilibrium Binding Constants for Tetracycline Analogs with the Tet Repressor", *Antimicrobial Agents and Chemotherapy*, vol. 35, No. 8, pp. 1591–1595.

Baim, S.B., et al., (1991) "A chimeric mammalian transactivator based on the lac repressor that is regulated by temperature and isopropyl β–D–thiogalactopyranoside", *Proceedings of the National Academy of Science*, vol. 88, pp. 5072–5076.

Gatz, C., et al., (1991) "Regulation of a modified CaMV 35S promoter by the Tn 10–encoder Tet receptor in transgenic tobacco", *Mol. Gen. Genet.*, vol. 227, No. 2, pp. 229–237.

Wissmann, A., et al., (1991) "Selection for Tn10 Tet Repressor Binding to tet Operator in *Escherichia coli*: Isolation of Temperature–Sensitive Mutants and Combinatorial Mutagenesis in the DNA Binding Motif", *Genetics*, vol. 128, pp. 225–232.

Labow, M.A., et al., (1990) "Conversion of the lac Repressor into an Allosterically Regulated Transcriptional Activator for Mammalian Cells", *Molecular and Cellular Biology*, vol. 10, No. 7, pp. 3343–3356.

Deuschle, U., et al., (1989) "Regulated expression of foreign genes in mammalian cells under the control of coliphage T3 RNA polymerase and lac repressor", *Proceedings of the National Academy of Science*, vol. 86, pp. 5400–5404.

Capecchi, M.R., (1989) "Altering the Genome by Homologous Recombination", *Science*, vol. 244, pp. 1288–1292.

Mermod, N., et al., (1989), "The Proline–Rich Transcriptional Activator of CTF/NF–I Is Distinct from the Replication and DNA Binding Domain", *Cell*, vol. 58, 741–753.

Mansour, S.L., et al., (1989) "Disruption of the proto–oncogene int–2 in mouse embryo–derived stem cells: a general strategy for targeting mutations to non–selectable genes", *Nature*, vol. 336, pp. 348–352.

Gatz, C., and Quail, P.H., (1988) "Tn10–encoded tet repressor can regulate an operator–containing plant promoter", *Proceedings of the National Academy of Science*, vol. 85, pp. 1394–1397.

Figge, J., et al., (1988) "Stringent Regulation of Stably Integrated Chloramphenicol Acetyl Transferase Genes by *E. coli* lac Repressor in Monkey Cells", *Cell*, vol. 52, 713–722.

Triezenberg, S.J., et al., (1988) "Functional dissection of VP16, the trans–activator of herpes simplex virus immediate early gene expression", *Genes & Development*, vol. 2, pp. 718–729.

Courey, A.J., and Tijan, R., (1988) "Analysis of Sp1 In Vivo Reveals Multiple Transcriptional Domains, Including a Novel Glutamine–Rich Activation Motif", *Cell*, vol. 55, pp. 887–898.

Tovar, K., et al., (1988) "Identification and nucleotide sequence of the class E tet regulatory elements and operator and inducer binding of the encoded purified Tet repressor", *Mol. Gen. Genet.*, vol. 215, pp. 76–80.

Altschmied, L. et al., (1988) "A threonine to alanine exchange at position 40 of Tet repressor alters the recognition of the sixth base pair of tet operator from GC to AT", *The EMBO Journal*, vol. 7, No. 12, pp. 4011–4017.

Brown, M., et al., (1987) "lac Repressor Can Regulate Expression from a Hybrid SV40 Early Promoter Containing a lac Operator in Animal Cells", *Cell*, vol. 49, pp. 603–612.

Hu,M.C–T and Davidson, N., (1987) "The Inducible lac Operator–Repressor System Is Functional in Mammalian Cells", *Cell*, vol. 46, pp. 555–566.

Smithies, O., et al., (1985) "Insertion of DNA sequences into the human chromosomal β–globin locus by homologous recombination", *Nature*, vol. 317, pp. 230–234.

Boshart, M., et al., (1985) "A Very Strong Enhancer Is Located Upstream of an Immediate Early Gene of Human Cytomegalovirus", *Cell*, vol. 41, No. 2, pp. 521–530.

Postle, K., et al., (1984) "Nucleotide sequence of the repressor gene of the TN10 tetracycline resistance determinant", *Nucleic Acid Research*, vol. 12, No. 12, pp. 4849–4863.

Unger, B., et al., (1984) "Nucleotide sequence of the gene, protein purification and characterization of the pSC101–encoded tetracycline resistance–gene–repressor", *Gene*, vol. 31, pp. 103–108.

Unger, B., et al., (1984) "Nucleotide sequence of the repressor gene of the RA1 tetracycline resistance determinant structural and functional comparison with three related Tet repressor genes", *Nucleic Acid Research*, vol. 12, No. 20, pp. 7693–7703.

Waters, S.H., et al., (1983) "The tetracycline resistance determinants of RP1 and Tn1721: nucleotide sequence analysis", *Nucleic Acid Research*, vol. 11, No. 17, pp. 6089–6105.

Hillen, W., and Schollmeier, K., (1983) "Nucleotide sequence of the Tn10 encoded tetracycline resistance gene", *Nucleic Acid Research*, vol. 11, No. 2, pp. 525–539.

```
5'  TGC ATT CGG ACG AGG TTA GCT ATG GCT GAA GAC AAC CAC AAA AAA ACA GTT   54
     C   I   R   T   R   L   A   M   A   E   D   N   H   K   K   T   V

AAG ATG TTG GAA TAC CTG GGC AAA GAT GTT CTT CAT GGT GTT TTT AAT TAT TTG  108
     K   M   L   E   Y   L   G   K   D   V   L   H   G   V   F   N   Y   L

GCA AAA CAC GAT GTT ACA TTG CTG GGC AAA GAG AAG AAA TAT TAT GAT   162
     A   K   H   D   V   T   L   L   G   E   E   K   K   Y   Y   D

ACC AAA ATT GAA GAC AAG GCC CTG AAC TTG GTA GAC TCT TTG GAA AGA ATC GCG  216
     T   K   I   E   D   K   A   L   N   L   V   D   S   L   E   R   I   A

TGG TCA AAT GTT TAC CCA AAT CGA ACT TCT CAA TAT GGA CCA AAA GAT CAC CAG  270
     W   S   N   V   Y   P   N   R   T   S   Q   Y   G   P   K   D   H   Q

TGT AAA TCT TCT GCA AAT GAA TTC GGA CCA GAG TCA GCA GAA TCT ACA   324
     C   K   S   S   A   N   E   F   G   P   E   S   A   E   S   T

AAT ATA AAA CTT CCA CGT AAA GAA TTC CTG AGA CTG TGT AAA AAA AAT  378
     N   I   K   L   P   R   K   E   F   L   R   L   C   K   K   N

CAT GAT GAG ATC TAT CCA ATA AAA AAG AGA GAG GAC CGC AGA CGC CTG GCT CTC  432
     H   D   E   I   Y   P   I   K   K   R   E   D   R   R   R   L   A   L

```
        1           2      3          4
        ●          ● ●         ●  ●●  ●
MSRLDKSKVINSALELLNEVGIEGLTTRKLAQKLGVEQPTLYWHVKNKRALLDALAIEMLDRH    63  B
MA--NRES--DA--G----T--DE-----------I------------------V-I-A--        D
MTK-QPNT--RA--D----VD--------ER---Q--A----FR----------EA--AEN        A
MNK-QREA--RT--G---D--M-------R-ER---Q--A----F---------EA--TIN        C
MTK---GT--AAG---------MDS------ER-K-Q--A----FQ--------PEA--RER       G
MA--SLDD--SM--T--DSE-L----------S-KI-----------R--QT-MNM-SEAI-AK-    E
```

```
              5           6          7
●●  ●  ●    ●   ●●  ●    ●  ●●●●●●●●●●●  ●  ●● ●●
HTHFCPLEGESWQDFLRNNAKSFRCALLSHRDGAKVHLGTRPTEKQYETLENQLAFLCQQGFS   126  B
-DYSL-AA-----S------M--R--RY------------D-----D-V-T--R-MTEN---        D
---SV-RADDD-RS--IG--R---Q---AY----RI-A----GAP-M--ADA--R---EA---       A
---ST-RDDDD-RS--KG--C---R---AY----RI-A----AAP-M-KADA--R---DA---       C
--RSL-E-N-D-RV--KE--L---T----Y----RI-A-----PNFG-A-T-IR---AE--C        G
--RSA--PT----Q--QE--L---K---V-----RL-I--S--PP-F-QA-A--RC--DA---       E
```

```
           8                              9
    ●  ●  ●● ●●●●●●  ●●  ●  ●         ●  ●● ●●●
LENALYALSAVGHFTLGCVLEDQEHQVAKEERE    TPTTDSMPPLLRQAIELFDHQGA    182  B
-RDG---I----S-----A---Q---TA-LTD-P   AAPDENL-----E-LQIM-SDDG    182  D
AGD-VN--MTISY--V-A---E-AGDSESG--GG   -VEQAPLS----A--DA--EA-P    183  A
AGD-T---H-ISY--V-A---Q-ASEADA---GEDQL-TSAST--AR-QS-MKIVYEA-P    186  C
PKR-VW--R--S-YVV-S---Q-ASDAD    --VPDRPDVSEQAPSSF-HVLFHELETD-M   184  G
V-E--FI-QSIS------A---E-ATNQIENNHV    I-AA----QE-FNIQARTS-      179  E
```

```
       10
        ●
EPAFLFGLELIICGLEKQLKCESGS                207  B
-Q---H---SL-R-F-V--TALLQIVGGDKLIIPFC      218  D
DA--EQ--AV-VD--A-RRLVVRNVEGPRKGDD         216  A
DA--ER--A---G----MRLTTNDIEVLKNVDE         219  C
DA--N---DSL-A-F-RLRAAVLATD                210  G
-M--H---KSL-F-FSA--DEKKHTPIEDGNK          211  E
```

5' <u>GAATTC</u>GGGG
EcoRI  +75

CCGCGGAGGCTGGATCGGTCCCGGTGTCTTCTATGGAGGTCAAAACAGCGTGGA

+1
←
 C                                                              P<sub>hCMV*-3</sub>
TGGCGTCTCCAGGCGATCTGACGGTTCACTAAACGAGCTCTGCTT ATATAGG
                                                                                   -31

*tet O*
TC ( *GAGTTTACCACTCCCTATCAGTGATAGAGAAAAGTGAAAGTC* )₇GAGC
         →         ←

P<sub>hCMV*-1</sub>
TCGGTACCCGGGTCGAGTAGGCGTGTACGGTGGGAGGCCTATATAAGCAGAG
                -53

CTCGTTTAGTGAACCGTCAGATCGCCTGGAGACGCCATCCACGCTGTTTGA
                                    +1 →

CCTCCATAGAAGACACCGGGACCGATCCAGCCTCCGCGGCCCC<u>GAATTC</u> 3'
                                                                                     +75     EcoRI

FIG. 7B

```
                                        +19
                              5' AGATCTGCAGGGTCGC
                                 Bgl II    Pst I

+1
 ←┐                          P_K*-37              -37
  A
TCGGTGTTCGAGGCCACACGCGTCACCTT AATATGCGAAGTGGACCGGATC tetO
TC ( GAGTTTACCACTCCCTATCAGTGATAGAGAAAAGTGAAAGTC )₇GAGC
     ────────────────────→ ←────────────

P_hCMV*-1
TCGGTACCCGGGTCGAGTAGGCGTGTACGGTGGGAGGCCTATATAAGCAGAG
      -53

CTCGTTTAGTGAACCGTCAGATCGCCTGGAGACGCCATCCACGCTGTTTTGA
                └──→
                 +1

CCTCCATAGAAGACACCGGGACCGATCCAGCCTCCGCGGCCCCGAATTC  3'
                                           +75   EcoRI
```

TETRACYCLINE-INDUCIBLE TRANSCRIPTIONAL ACTIVATOR AND TETRACYCLINE-REGULATED TRANSCRIPTION UNITS

RELATED APPLICATIONS

This application is a continuation-in-part of U.S patent application Ser. No. 08/270,637, filed Jul. 1, 1994, now abandoned.

BACKGROUND OF THE INVENTION

Functional analysis of cellular proteins is greatly facilitated through changes in the expression level of the corresponding gene for subsequent analysis of the accompanying phenotype. For this approach, an inducible expression system controlled by an external stimulus is desirable. Ideally such a system would not only mediate an "on/off" status for gene expression but would also permit limited expression of a gene at a defined level.

Attempts to control gene activity have been made using various inducible eukaryotic promoters, such as those responsive to heavy metal ions (Mayo et al. (1982) *Cell* 29:99–108; Brinster et al. (1982) *Nature* 296:39–42; Searle et al. (1985) *Mol. Cell. Biol.* 5:1480–1489), heat shock (Nouer et al. (1991) in *Heat Shock Response*, e.d. Nouer, L., CRC, Boca Raton, Fla., pp 167–220) or hormones (Lee et al. (1981) *Nature* 294:228–232; Hynes et al. (1981) *Proc. Natl. Acad. Sci. U.S.A.* 78:2038–2042; Klock et al. (1987) *Nature* 329:734–736; Israel & Kaufman (1989) *Nucl. Acids Res.* 17:2589–2604). However, these systems have generally suffered from one or both of the following problems: (1) the inducer (e,g, heavy metal ions, heat shock or steroid hormones) evokes pleiotropic effects, which can complicate analyses, and (2) many promoter systems exhibit high levels of basal activity in the non-induced state, which prevents shut-off the regulated gene and results in modest induction factors.

An approach to circumventing these limitations is to introduce regulatory elements from evolutionarily distant species such as *E. coli* into higher eukaryotic cells with the anticipation that effectors which modulate such regulatory circuits will be inert to eukaryotic cellular physiology and, consequently, will not elicit pleiotropic effects in eukaryotic cells. For example, the Lac repressor (lacR)/operator/inducer system of *E. coli* functions in eukaryotic cells and has been used to regulate gene expression by three different approaches: (1) prevention of transcription initiation by properly placed lac operators at promoter sites (Hu & Davidson (1987) *Cell* 48:555–566; Brown et al. (1987) *Cell* 49:603–612; Figge et al. (1988) *Cell* 52:713–722; Fuerst et al. (1989) *Proc. Natl. Acad. Sci. U.S.A.* 86:2549–2553: Deuschle et al. (1989) *Proc. Natl. Acad. Sci. U.S.A.* 86:5400–5405); (2) blockage of transcribing RNA polymerase II during elongation by a LacR/operator complex (Deuschle et al. (1990) *Science* 248:480–483); and (3) activation of a promoter responsive to a fusion between LacR and the activation domain of herpes simples virus (HSV) virion protein 16 (VP16) (Labow et al. (1990) *Mol. Cell. Biol.* 10:3343–3356; Baim et al. (1991) *Proc. Natl. Acad. Sci. U.S.A.* 88:5072–5076).

In one version of the Lac system, expression of lac operator-linked sequences is constitutively activated by a LacR-VP16 fusion protein and is mined off in the presence of isopropyl-β-D-thiogalactopyranoside (IPTG) (Labow et al. (1990), cited supra). In another version of the system, a lacR-VP16 variant is used which binds to lac operators in the presence of IPTG, which can be enhanced by increasing the temperature of the cells (Baim et al. (1991), cited supra). The utility of these lac systems in eukaryotic cells is limited, in part, because IPTG acts slowly and inefficiently in eukaryotic cells and must be used at concentrations which approach cytotoxic levels. Alternatively, use of a temperature shift to induce gene expression is likely to elicit pleiotropic effects in the cells. Thus, there is a need for a more efficient inducible regulatory system which exhibits rapid and high level induction of gene expression and in which the inducer is tolerated by eukaryotic cells without cytotoxicity or pleiotropic effects.

Components of the tetracycline (Tc) resistance system of *E. coli* have also been found to function in eukaryotic cells and have been used to regulate gene expression. For example, the Tet repressor (TetR), which binds to tet operator sequences in the absence of tetracycline and represses gene transcription, has been expressed in plant cells at sufficiently high concentrations to repress transcription from a promoter containing tet operator sequences (Gatz, C. et al. (1992) *Plant J.* 2:397–404). However, very high intracellular concentrations of TetR are necessary to keep gene expression down-regulated in cells, which may not be achievable in many situations, thus leading to "leakiness" in the system.

In other studies, TetR has been fused to the activation domain of VP16 to create a tetracycline-controlled transcriptional activator (tTA) (Gossen, M. and Bujard, H. (1992) *Proc. Natl. Acad. Sci. U.S.A.* 89:5547–5551). The tTA fusion protein is regulated by tetracycline in the same manner as TetR, i.e., tTA binds to tet operator sequences in the absence of tetracycline but not in the presence of tetracycline. Thus, in this system, in the continuous presence of Tc, gene expression is kept off, and to induce transcription, Tc is removed.

SUMMARY OF THE INVENTION

This invention pertains to an inducible regulatory system which utilizes components of the Tet repressor/operator/inducer system of prokaryotes to stimulate gene expression in eukaryotic cells. In the system of the invention, transcription of a tet operator-linked nucleotide sequence is kept silent in the absence of tetracycline but can be rapidly and strongly induced in the presence of tetracycline (or analogue thereof). Transcription is induced by a fusion protein composed of at least two polypeptides, a first polypeptide which binds to tet operator sequences in the presence of tetracycline or a tetracycline analogue and a second polypeptide which directly or indirectly activates transcription in eukaryotic cells. In a preferred embodiment, the first polypeptide of the fusion protein is a mutated Tet repressor which is regulated by Tc in a reverse manner from the wild type repressor, i.e., it binds to tet operator sequences in the presence rather than in the absence of Tc. Thus, in the absence of the inducing agent (Tc or a Tc analogue), transcription of a tet operator-linked nucleotide sequence remains uninduced. In the presence of the inducing agent, transcription of the tet operator-linked nucleotide sequence is stimulated by the transactivator fusion protein of the invention.

The inducible regulatory system of the invention has the advantageous properties that induction of gene expression is rapid, efficient and strong (e.g., typically between 1000 to 2000-fold; up to a 20,000-fold increase in expression has been observed) and the inducing agent does not have to be continuously present. Moreover, the inducing agent does not cause pleiotropic effects or cytotoxicity in eukaryotic cells. The inducible regulatory system of the invention can be applied to regulation of gene expression in cells either in vitro or in vivo, and may be particularly useful for gene therapy applications and for expression of gene products in transgenic and homologous recombinant organisms (e.g., animals and plants).

The inducible regulatory system of the invention involves at least two components: a tetracycline-inducible transcriptional activator and a target transcription unit to be regulated. Accordingly, one aspect of the invention pertains to a Tc-inducible transcriptional activator ("transactivator") fusion protein, and nucleic acid (e.g., DNA) encoding the fusion protein. A preferred fusion protein comprises a Tn10-encoded Tet repressor that is mutated at at least one amino acid position selected from amino acid positions 71, 95, 101 and/or 102, operatively linked to a herpes simplex virus virion protein 16 (VP 16) activation domain (the nucleotide and amino acid sequences of such a fusion protein are shown in SEQ ID NO: 1 and 2, respectively). In one embodiment, the activation domain of the fusion protein includes about 127 C-terminal amino acids of VP16 (e.g., the fusion protein of SEQ ID NO: 2). In another embodiment, the activation domain includes at least one copy of about 11 C-terminal amino acids of VP16 (e.g., the amino acid sequence of which is shown in SEQ ID NO: 4). Other mutated Tet repressors and transcriptional activation domains having the requisite functional activities are within the scope of the invention. Additionally, the transactivator fusion protein can include a third polypeptide which promotes transport of the fusion protein to a cell nucleus. For example, a nuclear localization signal (e.g., having an amino acid sequence shown in SEQ ID NO: 5) can be incorporated into the fusion protein. The invention further provides recombinant vectors and host cells comprising nucleic acid encoding a transactivator fusion protein of the invention. The invention still further provides transgenic and homologous recombinant organisms comprising nucleic acid encoding a transactivator fusion protein of the invention.

A transactivator of the invention is used to regulate the transcription of a target transcription unit composed of a nucleotide sequence to be transcribed operatively linked to a a minimal promoter sequence and at least one tet operator sequence. The nucleotide sequence to be transcribed may encode a protein of interest or an active RNA molecule (e.g., antisense RNA molecule or ribozyme) and may be an exogenous or endogenous nucleotide sequence. A first nucleic acid encoding a transactivator of the invention and a second nucleic acid comprising a target transcription unit for the transactivator can be incorporated into a nucleic acid composition. The nucleic acid composition can be introduced into host cells or organisms (e.g., transgenic and homologous recombinant animals and plants) to allow for tetracycline-inducible expression of the target nucleotide sequence to be transcribed.

In addition to providing a regulatory system for expression of a single nucleotide sequence to be transcribed, the invention also features novel target transcription units that enable coordinate or independent regulation of two or more nucleotide sequences to be transcribed. In one embodiment, coordinate regulation of two nucleotide sequences to be transcribed is achieved using a transcription unit in which a first nucleotide sequence to be transcribed is operatively linked to the 5' end of a tet operator sequence(s) and a second nucleotide sequence to be transcribed is operatively linked to the 3' end of the same tet operator sequence(s) such that the first and second nucleotide sequences are transcribed in a divergent manner. Suitable bidirectional promoters for such bidirectional transcription units are shown in SEQ ID NOs: 6 and 7. Such transcription units are particularly useful for producing stoichiometric amounts of two subunits of a heterodimeric protein (e.g., antibody chains) in the same cell or for coexpressing a gene of interest and a gene encoding a detectable marker in the same cell, thereby allowing for selection of cells expressing the gene of interest.

In another embodiment, independent regulation of two nucleotide sequences is achieved using a transcription unit in which a first nucleotides sequence to be transcribed is operatively linked to a tet operator of a first class type and a second nucleotides sequence to be transcribed is operatively linked to a tet operator of a second, different class type. Two different transcriptional activator fusion proteins are then used to regulate the transcription of the two nucleotide sequences: one fusion protein binds to the first class of tet operator. sequences in the presence of Tc, whereas the other fusion protein binds to the second class of tet operator sequences in the absence of Tc (or alternatively, the first fusion protein binds to the first class of tet operator sequences in the absence of Tc and the second fusion protein binds to the second class of tet operator sequences in the presence of Tc). This transcription unit is particularly useful for independently regulating expression of a therapeutic gene and a suicide gene in a host. For example, expression of the therapeutic gene is stimulated in the presence of tetracycline and then when the therapy is completed, expression of the suicide gene is stimulated by removing the tetracycline.

Another aspect of the invention pertains to methods for stimulating transcription of a nucleotide sequence operatively linked to at least one tet operator sequence in a host cell or animal which expresses a transactivator fusion protein of the invention. In a host cell, transcription is stimulated by contacting the cell with Tc or a Tc analogue. In a subject (e.g., transgenic or homologous recombinant organisms), transcription is stimulated by administering Tc or a Tc analogue to the subject. Different Tc analogues, and variation of the concentration of the inducing agent, can be used to modulate the level of induction of gene expression. Preferred Tc analogues for high level gene expression include anhydrotetracycline and doxycycline. The invention further provides a process for producing and isolating proteins of interest using the regulatory system of the invention is also provided.

Novel kits for regulating the expression of a gene of interest are also within the scope of the invention. The kits of the invention can include at least one nucleic acid molecule encoding a transactivator fusion protein of the invention and a target transcription unit into which a gene of interest can be cloned such that the gene is operatively linked to a tet operator sequence(s). Target transcription units into which multiple genes of interest can be cloned, e.g., for coordinate or independent regulation, can also be included in kits of the invention. Moreover, at least one tetracycline or tetracycline analogue may be included in the kits.

BRIEF DESCRIPTION OF THE DRAWINGS

FIG. 1 is a bar graph depicting the stimulation of luciferase activity in HR5-C11 cells by tetracycline and different tetracycline analogues (1 µg/ml f.c.). Cells were grown in the absence (−) or presence of the indicated tetracyclines for 3 days before luciferase activity was determined. Each solid and hatched bar represents the luciferase activity of a single culture dish.

FIG. 4 shows the amino acid sequences of various classes of Tet repressors, illustrating the homology between the amino acid sequences of different classes of Tet repressors, as compared to class B Tet repressors (e.g., Tn10-derived). Amino acid positions in other classes of Tet repressors that are identical to class B are indicated by a dash.

FIG. 5 shows the nucleotide sequences of tet operators of different classes: class A (SEQ ID NO: 11), class B (SEQ ID NO: 12), class C (SEQ ID NO: 13), class D (SEQ ID NO: 14) and class E (SEQ ID NO: 15).

FIG. 7A (SEQ ID NO: 6) shows the nucleotide sequence of a bidirectional promoter region for coordinate regulation of two genes of interest by a tetracycline-regulated transcriptional activator.

FIG. 7B (SEQ ID NO: 7) shows the nucleotide sequence of a bidirectional promoter region coordinate regulation of two genes of interest by a tetracycline-regulated transcriptional activator.

FIG. 9A illustrates self-regulation of expression of a wild-type Tet repressor-containing transactivator fusion protein that binds to tet operators in the absence of Tc. FIG. 9B illustrates self-regulation of expression of a mutated Tet repressor-containing transactivator fusion protein that binds to tet operators in the presence of Tc.

DETAILED DESCRIPTION OF THE INVENTION

Figure 2:
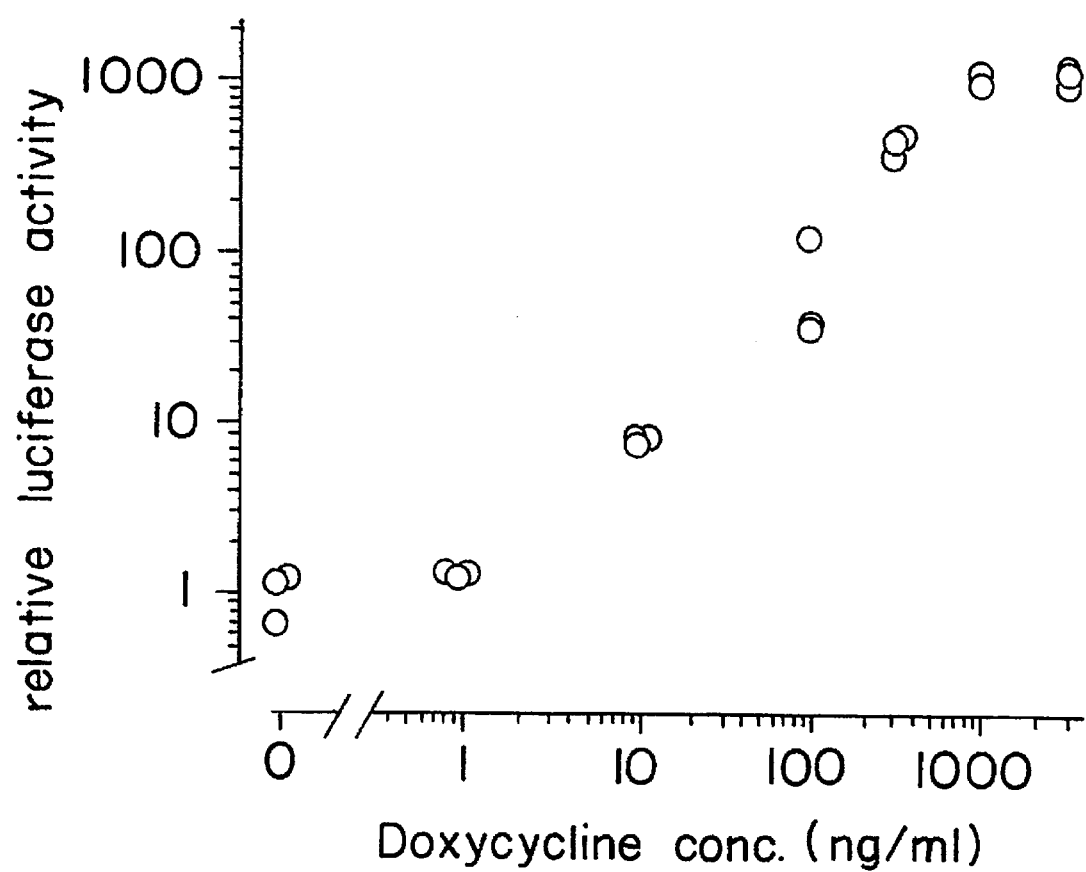
FIG. 2 is a graph depicting the relative luciferase activity in HR5-C 11 cells when incubated with different concentrations of doxycycline. The results of three independent experiments are shown.

This invention pertains to nucleic acid molecules and proteins which can be used to regulate the expression of genes in eukaryotic cells or animals in an inducible manner. Regulation of gene expression by the system of the invention involves at least two components: A gene which is operatively linked to a regulatory sequence and a protein which, in the presence of an inducible agent, binds to the regulatory sequence and activates transcription of the gene. The system of the invention utilizes components of the Tet repressor/operator/inducer system of prokaryotes to stimulate gene expression in eukaryotic cells. In particular, the invention pertains to a fusion protein which is capable of activating gene transcription when bound to tet operator sequences, but which binds to tet operator sequences only in the presence of tetracycline, or an analogue thereof. Thus, transcription of a gene operatively linked to a tet operator sequence(s) is induced by the fusion protein of the invention by addition of the inducing agent, i.e., tetracycline or an analogue thereof. In the absence of the inducing agent, gene transcription remains uninduced. The invention further pertains to target transcription units for regulation by a transactivator fusion protein of the invention. In addition to allowing for regulation of a single tet-operator linked gene of interest, the invention also provides novel transcription units containing two or more genes to be transcribed that can be regulated in either a coordinate or independent manner by a transactivator fusion protein of the invention. Methods for stimulating transcription of a gene using tetracycline (or analogues thereof) are also encompassed by the invention.

The nucleic acids and proteins comprising the components of the inducible regulatory system of the invention, and their interrelationship, are discussed in greater detail in the following subsections.

I. Tetracycline-Inducible Transcriptional Activators

In the inducible regulatory system of the invention, transcription of a gene is activated by a transcriptional activator protein, also referred to herein simply as a transactivator. The transactivator of the invention is a fusion protein. One aspect of the invention thus pertains to fusion proteins and nucleic acids (e.g., DNA) encoding fusion proteins. The term "fusion protein" is intended to describe at least two polypeptides, typically from different sources, which are operatively linked. With regard to the polypeptides, the term "operatively linked" is intended to mean that the two polypeptides are connected in manner such that each polypeptide can serve its intended function. Typically, the two polypeptides are covalently attached through peptide bonds. The fusion protein is preferably produced by standard recombinant DNA techniques. For example, a DNA molecule encoding the first polypeptide is ligated to another DNA molecule encoding the second polypeptide, and the resultant hybrid DNA molecule is expressed in a host cell to produce the fusion protein. The DNA molecules are ligated to each other in a 5' to 3' orientation such that, after ligation, the translational frame of the encoded polypeptides is not altered (i.e., the DNA molecules are ligated to each other in-frame).

A. The First Polypeptide of the Transactivator Fusion Protein

The transactivator fusion protein of the invention is composed, in part, of a first polypeptide which binds to a tet operator sequence in the presence of tetracycline (Tc), or an analogue thereof. The first polypeptide of the fusion protein is preferably a mutated Tet repressor. The term "mutated Tet repressor" is intended to include polypeptides having an amino acid sequence which is similar to a wild-type Tet repressor but which has at least one amino acid difference from the wild-type Tet repressor. The term "wild-type Tet repressor" is intended to describe a protein occurring in nature which represses transcription from tet operator sequences in prokaryotic cells in the absence of Tc. The amino acid difference(s) between a mutated Tet repressor and a wild-type Tet repressor may be substitution of one or more amino acids, deletion of one or more amino acids or addition of one or more amino acids. The mutated Tet repressor of the invention has the following functional properties: 1) the polypeptide can bind to a tet operator sequence, i.e., it retains the DNA binding specificity of a wild-type Tet repressor; and 2) it is regulated in a reverse manner by tetracycline than a wild-type Tet repressor, i.e., the mutated Tet repressor binds to a tet operator sequence only the presence of Tc (or Tc analogue) rather than in the absence of Tc.

In a preferred embodiment, a mutated Tet repressor having the functional properties described above is created by substitution of amino acid residues in the sequence of a wild-type Tet repressor. For example, as described in Example 1, a Tn10-derived Tet repressor having amino acid substitutions at amino acid positions 71, 95, 101 and 102 has the desired functional properties and thus can be used as the first polypeptide in the transactivator fusion protein of the invention. The amino acid sequence of this mutated Tet repressor is shown in SEQ ID NO: 2 (positions 1–207). In one embodiment of the mutated Tet repressor, position 71 is mutated from glutamic acid to lysine, position 95 is mutated from aspartic acid to asparagine, position 101 is mutated from leucine to serine and position 102 is mutated from glycine to aspartic acid, although the invention is not limited to these particular mutations. Mutation of fewer than all four of these amino acid positions may be sufficient to achieve a Tet repressor with the desired functional properties. Accordingly, a Tet repressor is preferably mutated at at least one of these positions. Other amino acid substitutions, deletions or additions at these or other amino acid positions which retain the desired functional properties of the mutated Tet repressor are within the scope of the invention. The crystal structure of a Tet repressor-tetracycline complex, as described in Hinrichs, W. et al. (1994) *Science* 264:418–420, can be used for rational design of mutated Tet repressors. Based upon this structure, amino acid position 71 is located outside the tetracycline binding pocket, suggesting mutation at this site may not be necessary to achieve the desired functional properties of a mutated Tet repressor of the invention. In contrast, amino acid positions 95, 101 and 102 are located within the conserved tetracycline binding pocket. Thus, the tetracycline binding pocket of a Tet repressor may be targeted for mutation to create a mutated Tet repressor of the invention.

Additional mutated Tet repressors for incorporation into a fusion protein of the invention can be created according to the teachings of the invention. A number of different classes of Tet repressors have been described, e.g., A, B, C, D and E (of which the Tn10 encoded repressor is a class B repressor). The amino acid sequences of the different classes of Tet repressors share a high degree of homology (i.e., 40–60% across the length of the proteins), including in the region encompassing the above-described mutations. The amino acid sequences of various classes of Tet repressors are shown and compared in FIG. 4, and are also described in Tovar, K. et al. (1988) *Mol. Gen. Genet.* 215:76–80. Accordingly, equivalent mutations to those described above for the Tn10-derived Tet repressor can be made in other classes of Tet repressors for inclusion in a fusion protein of the invention. For example, amino acid position 95, which is an aspartic acid in all five repressor classes, can be mutated to asparagine in any class of repressor. Similarly, position 102, which is glycine in all five repressor classes, can be mutated to aspartic acid in any class of repressor. Additional suitable equivalent mutations will be apparent to those skilled in the art and can be created and tested for functionality by procedures described herein. Nucleotide and amino acid sequences of Tet repressors of the A, C, D and E classes are disclosed in Waters, S. H. et al. (1983) *Nucl. Acids Res* 11:6089–6105, Unger, B. et al. (1984) *Gene* 31: 103–108, Unger, B. et al. (1984) *Nucl Acids Res.* 12:7693–7703 and Tovar, K. et al. (1988) *Mol. Gen. Genet.* 215:76–80, respectively. These wild-type sequences can be mutated according to the teachings of the invention for use in the inducible regulatory system described herein.

Alternative to the above-described mutations, additional suitable mutated Tet repressors (i.e., having the desired functional properties described above) can be created by mutagenesis of a wild type Tet repressor and selection as described in Example 1. The nucleotide and amino acid sequences of wild-type class B Tet repressors are disclosed in Hillen, W. and Schollmeier, K. (1983) *Nucl. Acids Res.* 11:525–539 and Postle, K. et al. (1984) *Nucl. Acids Res.* 12:4849–4863. The nucleotide and amino acid sequences of wild-type class A, C, D and E type repressors are cited above. A mutated Tet repressor can be created and selected, for example as follows: a nucleic acid (e.g., DNA) encoding a wild-type Tet repressor is subjected to random mutagenesis and the resultant mutated nucleic acids are incorporated into an expression vector and introduced into a host cell for screening. A screening assay is used which allows for selection of a Tet repressor which binds to a tet operator sequence only in the presence of tetracycline. For example, a library of mutated nucleic acids in an expression vector can be introduced into an *E. coli* strain in which tet operator sequences control the expression of a gene encoding a Lac repressor and the Lac repressor controls the expression of a gene encoding an selectable marker (e.g., drug resistance). Binding of a Tet repressor to tet operator sequences in the bacteria will inhibit expression of the Lac repressor, thereby inducing expression of the selectable marker gene. Cells expressing the marker gene are selected based upon the selectable phenotype (e.g., drug resistance). For wild-type Tet repressors, expression of the selectable marker gene will occur in the absence of Tc. A nucleic acid encoding a mutated Tet repressor is selected using this system based upon the ability of the nucleic acid to induce expression of the selectable marker gene in the bacteria only in the presence of Tc.

A first polypeptide of the transactivator fusion protein (e.g., the mutated Tet repressor) has the property of binding specifically to a tet operator sequence. Each class of Tet repressor has a corresponding target tet operator sequence. Accordingly, the term "tet operator sequence" is intended to encompass all classes of tet operator sequences, e.g. class A, B, C, D, and E. Nucleotide sequences of these five classes of tet operators are shown in FIG. 5 and SEQ ID NOs: 11–15, and are described in Waters, S. H. et al. (1983) cited supra, Hillen, W. and Schollenmeier, K. (1983) cited supra, Stüber, D. and Bujard, H. (1981) *Proc. Natl. Acad. Sci. U.S.A.* 78:167–171, Unger, B. et al. (1984) cited supra and Tovar, K. et al. (1988) cited supra. In a preferred embodiment, the mutated Tet repressor is a Tn10-encoded repressor (i.e., class B) and the tet operator sequence is a class B tet operator sequence. Alternatively, a mutated class A Tet repressor can be used with a class A tet operator sequence, and so on for the other classes of Tet repressor/operators.

Another approach for creating a mutated Tet repressor which binds to a class A tet operator is to further rotate the already mutated Tn10-derived Tet repressor described herein (a class B repressor) such that it no longer binds efficiently to a class B type operator but instead binds efficiently to a class A type operator. It has been found that nucleotide position 6 of class A or B type operators is the critical nucleotide for recognition of the operator by its complimentary repressor (position 6 is a G/C pair in class B operators and an A/T pair in class A operators) (see Wissman et al. (1988) *J. Mol. Biol.* 202:397–406). It has also been found that amino acid position 40 of a class A or class B Tet repressor is the critical amino acid residue for recognition of position 6 of the operator (amino acid position 40 is a threonine in class B repressors but is an alanine in class A repressors). It still further has been found that substitution of Thr40 of a class B repressor with Ala alters its binding specificity such that the repressor can now bind a class A operator (similarly, substitution of Ala40 of a class A repressor with Thr alters its binding specificity such that the repressor can now bind a class B operator) (see Altschmied et al. (1988) *EMBO J.* 7:4011–4017). Accordingly, one can alter the binding specificity of the mutated Tn10-derived Tet repressor disclosed herein by additionally changing amino acid residue 40 from Thr to Ala by standard molecular biology techniques (e.g., site directed mutagenesis).

A mutated Tet repressor having specific mutations (e.g., at positions 71, 95, 101 and/or 102, as described above) can be created by introducing nucleotide changes into a nucleic acid encoding a wild-type repressor by standard molecular biology techniques, e.g. site directed mutagenesis or PCR-mediated mutagenesis using oligonucleotide primers incorporating the nucleotide mutations. Alternatively, when a mutated Tet repressor is identified by selection from a library, the mutated nucleic acid can be recovered from the library vector. To create a transactivator fusion protein of the invention, a nucleic acid encoding a mutated Tet repressor is then ligated in-frame to another nucleic acid encoding a transcriptional activation domain and the fusion construct is incorporated into a recombinant expression vector. The transactivator fusion protein can be expressed by introducing the recombinant expression vector into a host cell or animal.

B. The Second Polypeptide of the Transactivator Fusion Protein

The first polypeptide of the transactivator fusion protein is operatively linked to a second polypeptide which directly or indirectly activates transcription in eukaryotic cells. To operatively link the first and second polypeptides, typically nucleotide sequences encoding the first and second polypeptides are ligated to each other in-frame to create a chimeric gene encoding a fusion protein, although the first and second polypeptides can be operatively linked by other means that preserve the function of each polypeptide (e.g., chemically crosslinked). In a preferred embodiment, the second polypeptide of the transactivator itself possesses transcriptional activation activity (i.e., the second polypeptide directly activates transcription). In another embodiment, the second polypeptide activates transcription by an indirect mechanism, through recruitment of a transcriptional activation protein to interact with the fusion protein. Accordingly, the term "a polypeptide which activates transcription in eukaryotic cells" as used herein is intended to include polypeptides which either directly or indirectly activates transcription.

Polypeptides which can function to activate transcription in eukaryotic cells are well known in the art. In particular, transcriptional activation domains of many DNA binding proteins have been described and have been shown to retain their activation function when the domain is transferred to a heterologous protein. A preferred polypeptide for use in the fusion protein of the invention is the herpes simplex virus virion protein 16 (referred to herein as VP16, the amino acid sequence of which is disclosed in Triezenberg, S. J. et al. (1988) *Genes Dev.* 2:718–729). In one embodiment, about 127 of the C-terminal amino acids of VP16 are used. For example, a polypeptide having an amino acid sequence shown in SEQ ID NO: 2 (positions 208–335) can be used as the second polypeptide in the fusion protein. In another embodiment, at least one copy of about 11 amino acids from the C-terminal region of VP16 which retain transcriptional activation ability is used as the second polypeptide. Preferably, a dimer of this region (i.e., about 22 amino acids) is used. Suitable C-terminal peptide portions of VP16 are described in Seipel, K. et al. (*EMBO J.* (1992) 13:4961–4968). For example, a dimer of a peptide having an amino acid sequence shown in SEQ ID NO: 4 (encoded by a nucleotide sequence shown in SEQ ID NO: 3) can be used as the second polypeptide in the fusion protein.

Other polypeptides with transcriptional activation ability in eukaryotic cells can be used in the fusion protein of the invention. Transcriptional activation domains found within various proteins have been grouped into categories based upon similar structural features. Types of transcriptional activation domains include acidic transcription activation domains, proline-rich transcription activation domains, serine/threonine-rich transcription activation domains and glutamine-rich transcription activation domains. Examples of acidic transcriptional activation domains include the VP 16 regions already described and amino. acid residues 753–881 of GAL4. Examples of proline-rich activation domains include amino acid residues 399–499 of CTF/NF 1 and amino acid residues 31–76 of AP2. Examples of serine/threonine-rich transcription activation domains include amino acid residues 1–427 of ITF1 and amino acid residues 2–451 of ITF2. Examples of glutamine-rich activation domains include amino acid residues 175–269 of Oct1 and amino acid residues 132–243 of Spl. The amino acid sequences of each of the above described regions, and of other useful transcriptional activation domains, are disclosed in Seipel, K. et al. (*EMBO J.* (1992) 13:4961–4968).

In addition to previously described transcriptional activation domains, novel transcriptional activation domains, which can be identified by standard techniques, are within the scope of the invention. The transcriptional activation ability of a polypeptide can be assayed by linking the polypeptide to another polypeptide having DNA binding activity and determining the amount of transcription of a target sequence that is stimulated by the fusion protein. For example, a standard assay used in the art utilizes a fusion protein of a putative transcriptional activation domain and a GAL4 DNA binding domain (e.g., amino acid residues 1–93). This fusion protein is then used to stimulate expression of a reporter gene linked to GAL4 binding sites (see e.g., Seipel, K. et ai. (1992) *EMBO J.* 11:4961–4968 and references cited therein).

In another embodiment, the second polypeptide of the fusion protein indirectly activates transcription by recruiting a transcriptional activator to interact with the fusion protein. For example, a mutated tetR of the invention can be fused to a polypeptide domain (e.g., a dimerization domain) capable of mediating a protein-protein interaction with a transcriptional activator protein, such as an endogenous activator present in a host cell. It has been demonstrated that functional associations between DNA binding domains and transactivation domains need not be covalent (see e.g., Fields and Song (1989) *Nature* 340:245–247; Chien et al. (1991) *Proc. Natl. Acad. Sci. U.S.A.* 88:9578–9582; Gyuris et al. (1993) *Cell* 75:791–803; and Zervos, A. S. (1993) *Cell* 72:223–232). Accordingly, the second polypeptide of the fusion protein may not directly activate transcription but rather may form a stable interaction with an endogenous polypeptide bearing a compatible protein-protein interaction domain and transactivation domain. Examples of suitable interaction (or dimerization) domains include leucine zippers (Landschulz et al. (1989) *Science* 243:1681–1688), helix-loop-helix domains (Murre, C. et al. (1989) *Cell* 58:537–544) and zinc finger domains (Frankel, A. D. et al. (1988) *Science* 240:70–73). Interaction of a dimerization domain present in the fusion protein with an endogenous nuclear factor results in recruitment of the transactivation domain of the nuclear factor to the fusion protein, and thereby to a tet operator sequence to which the fusion protein is bound.

C. A Third Polypeptide of the Transactivator Fusion Protein

In addition to a mutated Tet repressor and a transcriptional activation domain, a fusion protein of the invention can contain an operatively linked third polypeptide which promotes transport of the fusion protein to a cell nucleus. Amino acid sequences which, when included in a protein, function to promote transport of the protein to the nucleus are known in the art and are termed nuclear localization signals (NLS). Nuclear localization signals typically are composed of a stretch of basic amino acids. When attached to a heterologous protein (e.g., a fusion protein of the invention), the nuclear localization signal promotes transport of the protein to a cell nucleus. The nuclear localization signal is attached to a heterologous protein such that it is exposed on the protein surface and does not interfere with the function of the protein. Preferably, the NLS is attached to one end of the protein, e.g. the N-terminus. The amino acid sequence of a non-limiting example of an NLS that can be included in a fusion protein of the invention is shown in SEQ ID NO: 5. Preferably, a nucleic acid encoding the nuclear localization signal is spliced by standard recombinant DNA techniques in-frame to the nucleic acid encoding the fusion protein (e.g., at the 5' end).

The plasmid pUHD17-1 (described in further detail in Example 1), which comprises a transactivator of the invention having the nucleotide sequence shown in SEQ ID NO: 1, has been deposited on Jul. 8, 1994 under the provisions of the Budapest Treaty at the Deutsche Sammlung Von Mikroorganismen und ZellKulturen GmbH (DSM) in Braunschweig, Germany and assigned deposit number DSM 9279.

II. Expression of a Transactivator Fusion Protein

A. Expression Vectors

A nucleic acid of the invention encoding a transactivator fusion protein, as described above, can be incorporated into a recombinant expression vector in a form suitable for expression of the fusion protein in a host cell. The term "in a form suitable for expression of the fusion protein in a host cell" is intended to mean that the recombinant expression vector includes one or more regulatory sequences operatively linked to the nucleic acid encoding the fusion protein in a manner which allows for transcription of the nucleic acid into mRNA and translation of the mRNA into the fusion protein. The term "regulatory sequence" is art-recognized and intended to include promoters, enhancers and other expression control elements (e.g., polyadenylation signals). Such regulatory sequences are known to those skilled in the art and are described in Goeddel, Gene Expression Technology: Methods in Enzymology 185, Academic Press, San Diego, Calif. (1990). It should be understood that the design of the expression vector may depend on such factors as the choice of the host cell to be transfected and/or the amount of fusion protein to be expressed.

When used in mammalian cells, a recombinant expression vector's control functions are often provided by vital genetic material. For example, commonly used promoters are derived from polyoma, Adenovirus 2, cytomegalovirus and Simian Virus 40. Use of viral regulatory elements to direct expression of the fusion protein can allow for high level constitutive expression of the fusion protein in a variety of host cells. In a preferred recombinant expression vector, the sequences encoding the fusion protein are flanked upstream (i.e., 5') by the human cytomegalovirus IE promoter and downstream (i.e., 3') by an SV40 poly(A) signal. For example, an expression vector similar to that described in Example 1 can be used. The human cytomegalovirus IE promoter is described in Boshart et al. (1985) Cell 41:521–530. Other ubiquitously expressing promoters which can be used include the HSV-Tk promoter (disclosed in McKnight et al. (1984) Cell 37:253–262) and β-actin promoters (e.g., the human β-actin promoter as described by Ng et al. (1985) Mol. Cell. Biol. 5:2720–2732).

Alternatively, the regulatory sequences of the recombinant expression vector can direct expression of the fusion protein preferentially in a particular cell type, i.e., tissue-specific regulatory elements can be used. Non-limiting examples of tissue-specific promoters which can be used include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. U.S.A. 86:5473–5477), pancreas-specific promoters 0Edlund et al. (1985) Science 230:912–916), and mammary gland-specific promoters (e.g., milk whey promoter; U.S. Pat. No. 4,873,316 and European Application Publication No. 264,166). Developmentally-regulated promoters are also encompassed, for example the murine box promoters Kessel and Gruss (1990) Science 249:374–379) and the α-fetoprotein promoter (Campes and Tilghman (1989) Genes Dev. 3:537–546).

Figure 9A:
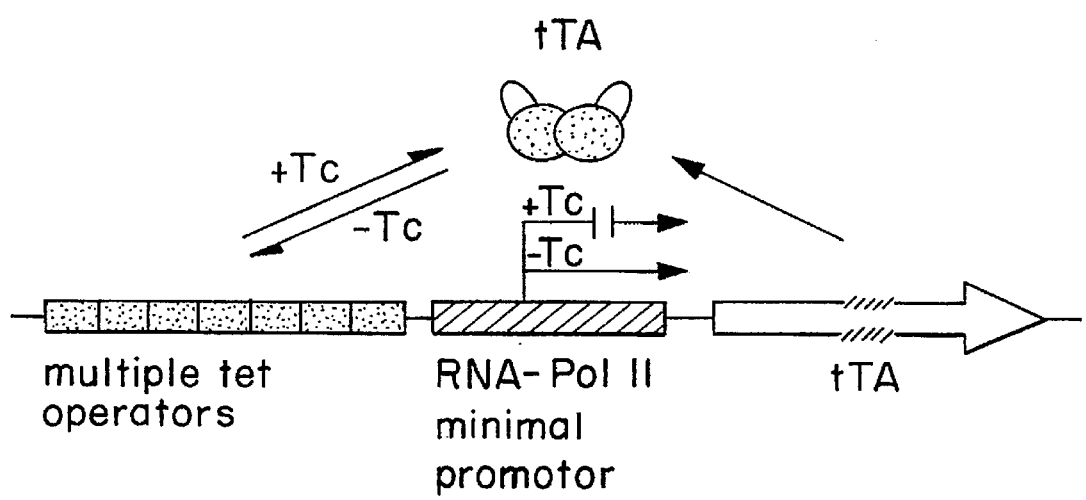
FIGS. 9A–9B are schematic diagrams of self-regulating promoters for expression of tetracycline-regulated transcriptional activators (tTA).
Figure 9B:
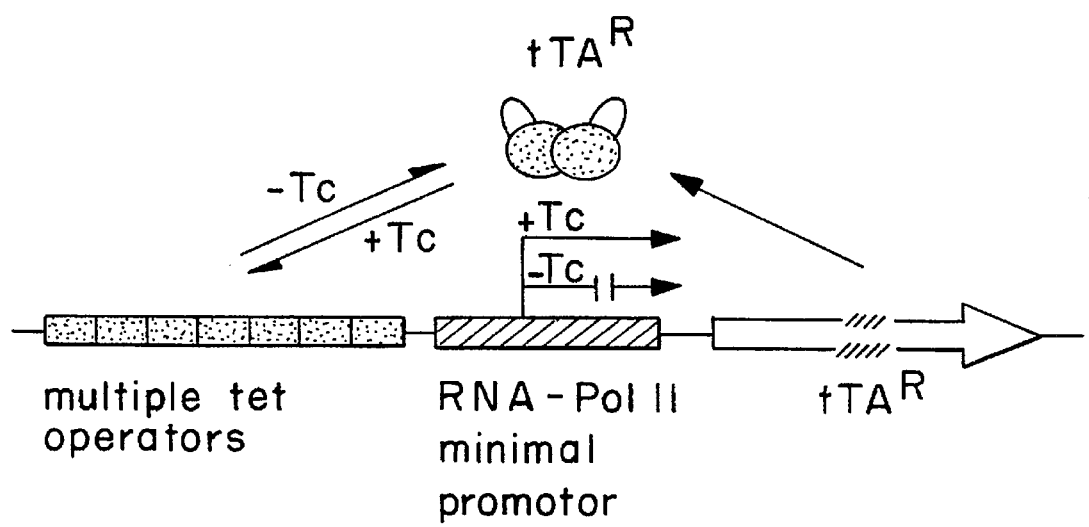

Alternatively, a self-regulating construct encoding a transactivator fusion protein can be created. To accomplish this, nucleic acid encoding the fusion protein is operatively linked to a minimal promoter sequence and at least one tet operator sequence. For example, the nucleic acid of SEQ ID NO: 1 can be linked to a promoter having a nucleotide sequence shown in SEQ ID NO: 8, 9 or 10 (the nucleic acids of SEQ ID NOs: 8 and 9 comprise a minimal CMV promoter and ten tet operators; the nucleic acids of SEQ ID NO: 10 comprises a TK promoter and ten tet operators). A schematic diagram of such a self-regulating construct is shown in FIG. 9B. When this nucleic acid is introduced into a cell (e.g., in a recombinant expression vector), a small amount of basal transcription of the transactivator gene is likely to occur due to "leakiness". In the presence of Tc (or analogue thereof) this small amount of the transactivator fusion protein will bind to the tet operator sequence(s) upstream of the nucleotide sequence encoding the transactivator and stimulate additional transcription of the nucleotide sequence encoding the transactivator, thereby leading to further production of the transactivator fusion protein in the cell. It will be appreciated by those skilled in the art that such a self-regulating promoter can also be used in conjunction with other tetracycline-regulated transactivators, such as the wild-type Tet repressor fusion protein (tTA) described in Gossen, M. and Bujard, H. (1992) Proc. Natl. Acad. Sci. U.S.A. 89:5547–5551, which binds to tet operators in the absence of Tc (as illustrated in FIG. 9A). When used in conjunction with this transactivator, self-regulated transcription of the nucleotide sequence encoding this transactivator is stimulated in the absence of Tc. The plasmid pUHD15-3, which comprises nucleotide sequences encoding the tTA described in Gossen and Bujard (1992), cited supra, operatively linked to a self-regulating promoter, has been deposited on Jul. 8, 1994 under the provisions of the Budapest Treaty at the Deutsche Sammlung Von Mikroorganismen und ZellKulturen GmbH (DSM) in Braunschweig, Germany and assigned deposit number DSM 9280.

In one embodiment, the recombinant expression vector of the invention is a plasmid, such as that described in Example 1. Alternatively, a recombinant expression vector of the invention can be a virus, or portion thereof, which allows for expression of a nucleic acid introduced into the viral nucleic acid. For example, replication defective retroviruses, adenoviruses and adeno-associated viruses can be used. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. The genome of adenovirus can be manipulated such that it encodes and expresses a transactivator fusion protein but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Alternatively, an adeno-associated virus vector such as that described in Tratschin et al. (1985) *Mol. Cell. Biol.* 5:3251–3260 can be used to express a transactivator fusion protein.

B. Host Cells

A fusion protein of the invention is expressed in a eukaryotic cell by introducing nucleic acid encoding the fusion protein into a host cell, wherein the nucleic acid is in a form suitable for expression of the fusion protein in the host cell. For example, a recombinant expression vector of the invention, encoding the fusion protein, is introduced into a host cell. Alternatively, nucleic acid encoding the fusion protein which is operatively linked to regulatory sequences (e.g., promoter sequences) but without additional vector sequences can be introduced into a host cell. As used herein, the term "host cell" is intended to include any eukaryotic cell or cell line so long as the cell or cell line is not incompatible with the protein to be expressed, the selection system chosen or the fermentation system employed. Non-limiting examples of mammalian cell lines which can be used include CHO dhfr⁻ cells (Urlaub and Chasin (1980) *Proc. Natl. Acad. Sci. U.S.A.* 77:4216–4220), 293 cells (Graham et al. (1977) *J. Gen. Virol.* 36: pp 59) or myeloma cells like SP2 or NS0 (Galfre and Milstein (1981) *Meth. Enzymol.* 73(B) :3–46).

In addition to cell lines, the invention is applicable to normal cells, such as cells to be modified for gene therapy purposes or embryonic cells modified to create a transgenic or homologous recombinant animal. Examples of cell types of particular interest for gene therapy purposes include hematopoietic stem cells, myoblasts, hepatocytes, lymphocytes, neuronal cells and skin epithelium and airway epithelium. Additionally, for transgenic or homologous recombinant animals, embryonic stem cells and fertilized oocytes can be modified to contain nucleic acid encoding a transactivator fusion protein. Moreover, plant cells can be modified to create transgenic plants.

The invention is broadly applicable and encompasses non-mammalian eukaryotic cells as well, including insect (e.g., *Sp. frugiperda*), yeast (e.g., *S. cerevisiae, S. pombe, P. pastoris, K. lactis, H. polymorpha*; as generally reviewed by Fleer, R. (1992) *Current Opinion in Biotechnology* 3(5) :486–496)), fungal and plant cells. Examples of vectors for expression in yeast S. cerivisae include p YepSec1 (Baldari. et al., (1987) *Embo J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.). The fusion protein can be expressed in insect cells using baculovirus expression vectors (e.g., as described in O'Reilly et al. (1992) *Baculovirus Expression Vectors: A Laboratory Manual*, Stockton Press). Baculovirus vectors available for expression of proteins in cultured insect cells (e.g., SF 9 cells) include the pAc series (Smith et al., (1983) *Mol. Cell Biol.* 3:2156–2165) and the pVL series (Lucklow, V. A., and Summers, M. D., (1989) *Virology* 170:31–39).

C. Introduction of Nucleic Acid into a Host Cell

Nucleic acid encoding the fusion protein can be introduced into a host cell by standard techniques for transfecting eukaryotic cells. The term "transfecting" or "transfection" is intended to encompass all conventional techniques for introducing nucleic acid into host cells, including calcium phosphate co-precipitation, DEAE-dextran-mediated transfection, lipofection, electroporation and microinjection. Suitable methods for transfecting host cells can be found in Sambrook et al. (*Molecular Cloning: A Laboratory Manual*, 2md Edition, Cold Spring Harbor Laboratory press (1989)), and other laboratory textbooks.

The number of host cells transformed with a nucleic acid of the invention will depend, at least in part, upon the type of recombinant expression vector used and the type of transfection technique used. Nucleic acid can be introduced into a host cell transiently, or more typically, for long term regulation of gene expression, the nucleic acid is stably integrated into the genome of the host cell or remains as a stable episome in the host cell. Plasmid vectors introduced into mammalian cells are typically integrated into host cell DNA at only a low frequency. In order to identify these integrants, a gene that contains a selectable marker (e.g., drug resistance) is generally introduced into the host cells along with the nucleic acid of interest. Preferred selectable markers include those which confer resistance to certain drugs, such as G418 and hygromycin. Selectable markers can be introduced on a separate plasmid from the nucleic acid of interest or, are introduced on the same plasmid. Host cells transfected with a nucleic acid of the invention (e.g., a recombinant expression vector) and a gene for a selectable marker can be identified by selecting for cells using the selectable marker. For example, if the selectable marker encodes a gene conferring neomycin resistance, host cells which have taken up nucleic acid can be selected with G418. Cells that have incorporated the selectable marker gene will survive, while the other cells die.

A host cell transfected with a nucleic acid encoding a fusion protein of the invention can be further transletted with one or more nucleic acids which serve as the target for the fusion protein. The target nucleic acid comprises a nucleotide sequence to be transcribed operatively linked to at least one tet operator sequence (described in more detail in Section III below).

Nucleic acid encoding the fusion protein of the invention can be introduced into eukaryotic cells growing in culture in vitro by conventional transfection techniques (e.g., calcium phosphate precipitation, DEAE-dextran transfection, electroporation etc.). Nucleic acid can also be transferred into cells in vivo, for example by application of a delivery mechanism suitable for introduction of nucleic acid into cells in vivo, such as retroviral vectors (see e.g., Ferry, N et al. (1991) *Proc. Natl. Acad. Sci. U.S.A.* 88:8377–8381; and Kay, M. A. et al. (1992) *Human Gene Therapy* 3:641–647), adenoviral vectors (see e.g., Rosenfeld, M. A. (1992) *Cell* 68:143–155; and Herz, J. and Gerard, R. D. (1993) *Proc. Natl. Acad. Sci. U.S.A.* 90:2812–2816), receptor-mediated DNA uptake (see e.g., Wu, G. and Wu, C. H. (1988) *J. Biol. Chem.* 263:14621; Wilson et al. (1992) *J. Biol. Chem.* 267:963–967; and U.S. Pat. No. 5,166,320), direct injection of DNA (see e.g., Acsadi et al. (1991) *Nature* 332: 815–818; and Wolff et al. (1990) *Science* 247:1465–1468) or particle bombardment (see e.g., Cheng, L. et al. (1993) *Proc. Natl. Acad. Sci. U.S.A.* 90:4455–4459; and Zelenin, A. V. et al. (1993) *FEBS Letters* 315:29–32). Thus, for gene therapy purposes, cells can be modified in vitro and administered to a subject or, alternatively, cells can be directly modified in vivo.

D. Transgenic Organisms

Nucleic acid a transactivator fusion protein can transferred into a fertilized oocyte of a non-human animal to create a transgenic animal which expresses the fusion protein of the invention in one or more cell types. A transgenic animal is an animal having cells that contain a transgene, wherein the transgene was introduced into the animal or an ancestor of the animal at a prenatal, e.g., an embryonic, stage. A transgene is a DNA which is integrated into the genome of a cell from which a transgenic animal develops and which remains in the genome of the mature animal, thereby directing the expression of an encoded gene product in one or more cell types or tissues of the transgenic animal. In one embodiment, the non-human animal is a mouse, although the invention is not limited thereto. In other embodiments, the transgenic animal is a goat, sheep, pig, cow or other domestic farm animal. Such transgenic animals are useful for large scale production of proteins (so called "gene pharming").

A transgenic animal can be created, for example, by introducing a nucleic acid encoding the fusion protein (typically linked to appropriate regulatory elements, such as a constitutive or tissue-specific enhancer) into the male pronuclei of a fertilized oocyte, e.g., by microinjection, and allowing the oocyte to develop in a pseudopregnant female foster animal. Intronic sequences and polyadenylation signals can also be included in the transgene to increase the efficiency of expression of the transgene. Methods for generating transgenic animals, particularly animals such as mice, have become conventional in the art and are described, for example, in U.S. Pat. Nos. 4,736,866 and 4,870,009 and Hogan, B. et al., (1986) *A Laboratory Manual*, Cold Spring Harbor, N.Y., Cold Spring Harbor Laboratory. A transgenic founder animal can be used to breed additional animals carrying the transgene. Transgenic animals carrying a transgene encoding the fusion protein of the invention can further be bred to other transgenic animals carrying other transgenes, e.g., to a transgenic animal which contains a gene operatively linked to a tet operator sequence (discussed in more detail in Section III below).

It will be appreciated that, in addition to transgenic animals, the regulatory system described herein can be applied to other transgenic organisms, such as transgenic plants. Transgenic plants can be made by conventional techniques known in the art. Accordingly, the invention encompasses non-human transgenic organisms, including animals and plants, that contains cells which express the transactivator fusion protein of the invention (i.e., a nucleic acid encoding the transactivator is incorporated into one or more chromosomes in cells of the transgenic organism).

E. Homologous Recombinant Organisms

The invention also provides a homologous recombinant non-human organism expressing the fusion protein of the invention. The term "homologous recombinant organism" as used herein is intended to describe an organism, e.g. animal or plant, containing a gene which has been modified by homologous recombination between the gene and a DNA molecule introduced into a cell of the animal, e.g., an embryonic cell of the animal. In one embodiment, the non-human animal is a mouse, although the invention is not limited thereto. An animal can be created in which nucleic acid encoding the fusion protein has been introduced into a specific site of the genome, i.e., the nucleic acid has homologously recombined with an endogenous gene.

To create such a homologous recombinant animal, a vector is prepared which contains DNA encoding the fusion protein flanked at its 5' and 3' ends by additional nucleic acid of a eukaryotic gene at which homologous recombination is to occur. The additional nucleic acid flanking that encoding the fusion protein is of sufficient length for successful homologous recombination with the eukaryotic gene. Typically, several kilobases of fling DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced DNA has homologously recombined with the endogenous DNA are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harbouring the homologously recombined DNA in their germ cells can be used to breed animals in which all cells of the animal contain the homologously recombined DNA. These "germline transmission" animals can further be mated to animals carrying a gene operatively linked to at least one tet operator sequence (discussed in more detail in Section III below).

In addition to the homologous recombination approaches described above, enzyme-assisted site-specific integration systems are known in the art and can be applied to the components of the regulatory system of the invention to integrate a DNA molecule at a predetermined location in a second target DNA molecule. Examples of such enzyme-assisted integration systems include the Cre recombinase-lox target system (e.g., as described in Baubonis, W. and Sauer, B. (1993) *Nucl. Acids Res.* 21:2025–2029; and Fukushige, S. and Sauer, B. (1992) *Proc. Natl. Acad. Sci. U.S.A.* 89:7905–7909) and the FLP recombinase-FRT target system (e.g., as described in Dang, D. T. and Perrimon, N. (1992) *Dev. Genet.* 13:367–375; and Fiering, S. et al. (1993) *Proc. Natl. Acad. Sci. U.S.A.* 90:8469–8473).

III. Target Transcription Units Regulated by a Tetracycline-Inducible Transactivator.

A fusion protein of the invention is used to regulate the transcription of a target nucleotide sequence. This target nucleotide sequence is operatively linked to a regulatory sequence to which the fusion protein binds. More specifically, the fusion protein regulates expression of a nucleotide sequence operatively linked to at least one tet operator sequence. Accordingly, another aspect of the invention relates to target nucleic acids (e.g., DNA molecules)

comprising a nucleotide sequence to be transcribed operatively linked to at least one tet operator sequence. Such nucleic acids are also referred to herein as tet-regulated transcription units (or simply transcription units).

Within a transcription unit, the "nucleotide sequence to be transcribed" typically includes a minimal promoter sequence which is not itself transcribed but which serves (at least in part) to position the transcriptional machinery for transcription. The minimal promoter sequence is linked to the transcribed sequence in a 5' to 3' direction by phosphodiester bonds (i.e., the promoter is located upstream of the transcribed sequence) to form a contiguous nucleotide sequence. Accordingly, as used herein, the terms "nucleotide sequence to be transcribed" or "target nucleotide sequence" are intended to include both the nucleotide sequence which is transcribed into mRNA and an operatively linked upstream minimal promoter sequence. The term "minimal promoter" is intended to describe a partial promoter sequence which defines the start site of transcription for the linked sequence to be transcribed but which by itself is not capable of initiating transcription efficiently, if at all. Thus, the activity of such a minimal promoter is dependent upon the binding of a transcriptional activator (such as the tetracycline-inducible fusion protein of the invention) to an operatively linked regulatory sequence (such as one or more tet operator sequences). In one embodiment, the minimal promoter is from the human cytomegalovirus (as described in Boshart et al. (1985) *Cell* 41:521–530). Preferably, nucleotide positions between about +75 to −53 and +75 to −31 are used. Other suitable minimal promoters are known in the art or can be identified by standard techniques. For example, a functional promoter which activates transcription of a contiguously linked reporter gene (e.g., chloramphenicol acetyl transferase, β-galactosidase or luciferase) can be progressively deleted until it no longer activates expression of the reporter gene alone but rather requires the presence of an additional regulatory sequence(s).

Within a transcription unit, the target nucleotide sequence (including the transcribed nucleotide sequence and its upstream minimal promoter sequence) is operatively linked to at least one tet operator sequence. In a typical configuration, the tet operator sequence(s) is operatively linked upstream (i.e., 5') of the minimal promoter sequence through a phosphodiester bond at a suitable distance to allow for transcription of the target nucleotide sequence upon binding of a regulatory protein (e.g., the transactivator fusion protein) to the tet operator sequence. That is, the transcription unit is comprised of, in a 5' to 3' direction: tet operator sequence(s)—a minimal promoter—a transcribed nucleotide sequence. It will be appreciated by those skilled in the art that there is some flexibility in the permissible distance between the tet operator sequence(s) and the minimal promoter, although typically the tet operator sequences will be located within about 200–400 base pairs upstream of the minimal promoter.

The nucleotide sequences of examples of tet-regulated promoters, containing tet operator sequences linked to a minimal promoter, that can be used in the invention are shown in SEQ ID NO: 8–10. The nucleotide sequences of SEQ ID NOs: 8 and 9 comprise a cytomegalovirus minimal promoter linked to ten tet operator sequences; the two nucleotide sequences differ in the distance between the operators and the first transcribed nucleotide. The nucleotide sequence of SEQ ID NO: 10 comprises a herpes simplex virus minimal tk promoter linked to ten tet operator sequences. The promoter of SEQ ID NO: 8 corresponds to $P_{hCMV}$*−1, described in Gossen, M. and Bujard, H. (1992) *Proc. Natl. Acad. Sci. U.S.A.* 89:5547–5551. The promoter of SEQ ID NO: 9 corresponds to $P_{hCMV}$*−2, also described in Gossen, M. and Bujard, H, cited supra.

Alternatively, since regulatory elements have been observed in the art to function downstream of sequences to be transcribed, it is likely that the tet operator sequence(s) can be operatively linked downstream (i.e., 3') of the transcribed nucleotide sequence. Thus, in this configuration, the transcription unit is comprised of, in a 5' to 3' direction: a minimal promoter—a transcribed nucleotide sequence—tet operator sequence(s). Again, it will be appreciated that them is likely to be some flexibility in the permissible distance downstream at which the tet operator sequence(s) can be linked.

The term "tet operator sequence" is intended to encompass all classes of tet operators (e.g., A, B, C, D and E). A nucleotide sequence to be transcribed can be operatively linked to a single tet operator sequence, or for an enhanced range of regulation, it can be operatively linked to multiple tet operator sequences (e.g., two, three, four, five, six, seven, eight, nine, ten or more operator sequences). In a preferred embodiment, the sequence to be transcribed is operatively linked to seven tet operator sequences.

A tet-regulated transcription unit can further be incorporated into a recombinant vector (e.g., a plasmid or viral vector) by standard recombinant DNA techniques. The transcription unit, or recombinant vector in which it is contained, can be introduced into a host cell by standard transfection techniques, such as those described above. It should be appreciated that, after introduction of the transcription unit into a population of host cells, it may be necessary to select a host cell clone which exhibit low basal expression of the tet operator-linked nucleotide sequence (i.e., selection for a host cell in which the transcription unit has integrated at a site that results in low basal expression of the tet operator-linked nucleotide sequence). Furthermore, a tet-regulated transcription unit can be introduced, by procedures described above, into the genome of a non-human animal at an embryonic stage or into plant cells to create a transgenic or homologous recombinant organism carrying the transcription unit in some or all of its cells. Again, it should be appreciated that it may be necessary to select a transgenic or homologous organism in which there is low basal expression of the tet operator-linked nucleotide sequence in cells of interest.

In one embodiment, the target nucleotide sequence of the tet-regulated transcription unit encodes a protein of interest. Thus, upon induction of transcription of the nucleotide sequence by the transactivator of the invention and translation of the resultant mRNA, the protein of interest is produced in a host cell or animal. Alternatively, the nucleotide sequence to be transcribed can encode for an active RNA molecule, e.g., an antisense RNA molecule or ribozyme. Expression of active RNA molecules in a host cell or animal can be used to regulate functions within the host (e.g., prevent the production of a protein of interest by inhibiting translation of the mRNA encoding the protein).

A transactivator of the invention can be used to regulate transcription of an exogenous nucleotide sequence introduced into the host cell or animal. An "exogenous" nucleotide sequence is a nucleotide sequence which is introduced into the host cell and typically is inserted into the genome of the host. The exogenous nucleotide sequence may not be present elsewhere in the genome of the host (e.g., a foreign nucleotide sequence) or may be an additional copy of a sequence which is present within the genome of the host but which is integrated at a different site in the genome. An exogenous nucleotide sequence to be transcribed and an operatively linked tet operator sequence(s) can be contained within a single nucleic acid molecule which is introduced into the host cell or animal.

Alternatively, a transactivator of the invention can be used to regulate transcription of an endogenous nucleotide sequence to which a tet operator sequence(s) has been linked. An "endogenous" nucleotide sequence is a nucleotide sequence which is present within the genome of the host. An endogenous gene can be operatively linked to a tet operator sequence(s) by homologous recombination. For example, a homologous recombination vector can be prepared which includes at least one tet operator sequence flanked on its 3' end by sequences representing the coding region of the endogenous gene and flanked on its 5' end by sequences from the upstream region of the endogenous gene by excluding the actual promoter region of the endogenous gene. The flanking sequences are of sufficient length for successful homologous recombination of the vector DNA with the endogenous gene. Preferably, several kilobases of flanking DNA are included in the homologous recombination vector. Homologous recombination in a host cell between the vector DNA and the endogenous gene results in replacement of a region of the endogenous promoter with one or more tet operator sequences. Thus, expression of the endogenous gene is placed under the control of the tet operator sequence(s).

A. Regulation of Expession of tet Operator-Linked Nucleotide Sequences

Expression of a tet operator-linked nucleotide sequences is regulated by a transactivator fusion protein of the invention. Thus, the fusion protein and the target nucleic acid are both present in a host cell or organism. The presence of both the transactivator fusion protein and the target transcription unit in the same host cell or organism can be achieved in a number of different ways. For example, a host cell can be transfected with one nucleic acid of the expression system (e.g., encoding the transactivator fusion protein), stably transfected cells can be selected and then the transfected cells can be re-transfected (also referred to as "supertransfected") with nucleic acid corresponding to the other nucleic acid of the expression system (e.g., the target nucleic acid to be transcribed). Two distinct selectable markers can be used for selection, e.g., uptake of the first nucleic acid can be selected with G418 and uptake of the second nucleic acid can be selected with hygromycin. Alternatively, a single population of cells can be transfected with nucleic acid corresponding to both components of the system. Accordingly, the invention provides a nucleic acid composition comprising:

a first nucleic acid encoding a fusion protein which activates transcription, the fusion protein comprising a first polypeptide which binds to a tet operator sequence in the presence of tetracycline or a tetracycline analogue operatively linked to a second polypeptide which activates transcription in enkaryotic cells; and a second nucleic acid comprising a nucleotide sequence to be transcribed operatively linked to at least one tet operator sequence.

In one embodiment, the two nucleic acids are two separate molecules (e.g., two different vectors). In this case, a host cell is cotransfected with the two nucleic acid molecules or successively transfected first with one nucleic acid molecule and then the other nucleic acid molecule. In another embodiment, the two nucleic acids are linked (i.e., colinear) in the same molecule (e.g., a single vector). In this case, a host cell is transfected with the single nucleic acid molecule.

The host cell may be a cell cultured in vitro or a cell present in vivo (e.g., a cell targeted for gene therapy). The host cell can further be a fertilized oocyte, embryonic stem cell or any other embryonic cell used in the creation of non-human transgenic or homologous recombinant animals. Transgenic or homologous recombinant animals which comprise both nucleic acid components of the expression system can be created by introducing both nucleic acids into the same cells at an embryonic stage, or more preferably, an animal which carries one nucleic acid component of the system in its genome is mated to an animal which carries the other nucleic acid component of the system in its genome. Offspring which have inherited both nucleic acid components can then be identified by standard techniques.

B. Coordinate Regulation of Expression of Two Nucleotide Sequences

In addition to providing a system for the regulated expression of a single transcribed nucleotide sequence, the invention further permits coordinated regulation of the expression of two nucleotide sequences operatively linked to the same tet operator sequence(s). Accordingly, another aspect of the invention pertains to a novel tet-regulated transcription unit for coordinate regulation of two genes. In this transcription unit, the same tet operator sequence(s) regulates the expression of two operatively linked nucleotide sequences that are transcribed in opposite directions from the common tet operator sequence(s). Accordingly, one nucleotide sequence is operatively linked to one side of the tet operator sequence (e.g., the 5' end on the top strand of DNA) and the other nucleotide sequence is operatively linked to the opposite side of the tet operator sequence (e.g., the 3' end on the top strand of DNA). Additionally, it should be understood that each nucleotide sequence to be transcribed includes an operatively linked minimal promoter sequence which is located between the nucleotide sequence to be transcribed and the tet operator sequence(s).

Figure 6:
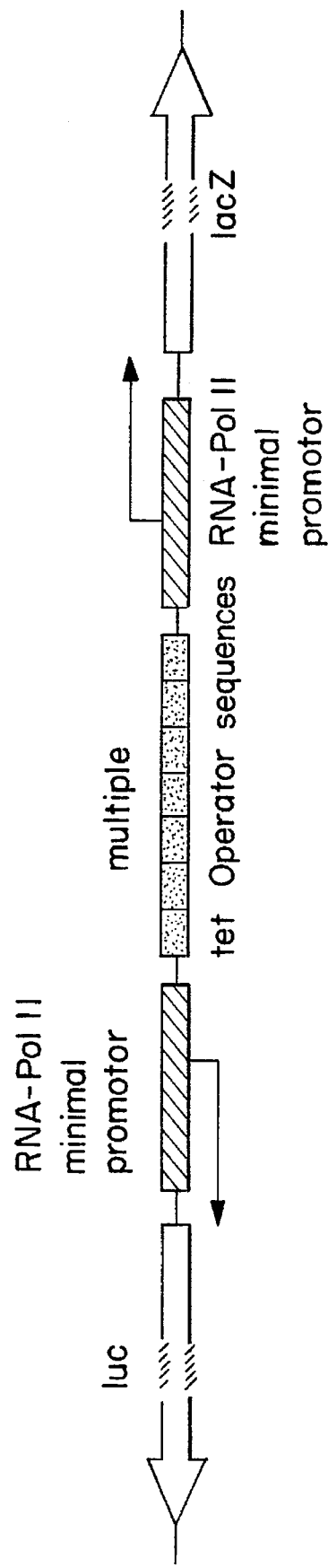
FIG. 6 is a schematic diagram of a bidirectional promoter construct for coordinate regulation of two genes of interest operatively linked to the same tet operators for regulation by a tetracycline-regulated transcriptional activator.

A representative example of such a transcription unit is diagrammed schematically in FIG. 6. In this vectors, the two nucleotide sequences, operatively linked to the same tet operator sequence(s), are transcribed in opposite directions relative to the tet operator sequence(s) (i.e., the sequences are transcribed in a divergent manner upon activation by a transactivator fusion protein of the invention). By "transcribed in opposite directions relative to the tet operator sequence(s)", it is meant that the first nucleotide sequence is transcribed 5' to 3' from one strand of the DNA (e.g., the bottom strand) and the second nucleotide sequence is transcribed 5' to 3' from the other stand of the DNA (e.g., the top strand), resulting in bidirectional transcription away from the tet operator sequence(s).

Accordingly, the invention provides a recombinant vector for coordinately-regulated, bidirectional transcription of two nucleotide sequence. In one embodiment, the vector comprises a nucleotide sequence linked by phosphodiester bonds comprising, in a 5' to 3' direction:

a first nucleotide sequence to be transcribed, operatively linked to at least one tet operator sequence, operatively linked to a second nucleotide sequence to be transcribed, wherein transcription of the first and second nucleotide sequences proceeds in opposite directions from the at least one tet operator sequence(s) (i.e., the first and second nucleotide sequences are transcribed in a divergent manner).

In another embodiment, the vector does not include the first and second nucleotide sequence to be transcribed but instead contains cloning sites which allow for the introduction into the vector of nucleotide sequences of interest.

Accordingly, in this embodiment, the vector comprises a nucleotide sequence comprising in a 5' to 3' direction:

a first cloning site for introduction of a first nucleotide sequence to be transcribed, operatively linked to at least one tet operator sequence, operatively linked to a second cloning site for introduction of a second nucleotide sequence to be transcribed, wherein transcription of a first and second nucleotide sequence introduced into the vector proceeds in opposite directions from the at least one tet operator sequence(s). It will be appreciated by those skilled in the art that this type of "cloning vector" may be in a form which also includes minimal promoter sequences such that a first nucleotide sequence introduced into the first cloning site is operatively linked to a first minimal promoter and a second nucleotide sequence introduced into the second cloning site is operatively linked to a second minimal promoter. Alternatively, the "cloning vector" may be in a form which does not include minimal promoter sequences and instead, nucleotide sequences including linked minimal promoter sequences are introduced into the cloning sites of the vector.

The term "cloning site" is intended to encompass at least one restriction endonuclease site. Typically, multiple different restriction endonuclease sites (e.g., a polylinker) are contained within the nucleic acid.

In yet another embodiment, the vector for coordinate, bidirectional transcription of two nucleotide sequences may contain a first nucleotide to be transcribed, such as that encoding a detectable marker (e.g., luciferase or β-galactosidase), and a cloning site for introduction of a second nucleotide sequence of interest.

The nucleotide sequences of two different suitable bidirectional promoter regions for use in a vector for coordinate regulation of two nucleotide sequences to be transcribed, as described herein, are shown in FIGS. 7A and 7B (SEQ ID NOS: 6 and 7, respectively). In the construct of FIG. 7A, both minimal promoters present in the construct are derived from a CMV promoter. In the construct of FIG. 7B, one minimal promoter present in the construct is derived from a CMV promoter, whereas the second minimal promoter is derived from a TK promoter. A plasmid pUHDG1316-8, comprising a bidirectional promoter of the invention, has been deposited on Jul. 8, 1994 under the provisions of the Budapest Treaty at the Deutsche Sammlung Von Mikroorganismen und ZellKulturen GmbH (DSM) in Braunschweig, Germany and assigned deposit number DSM 9281.

The transcription unit of the invention for bidirectional transcription of two nucleotide sequences operatively linked to the same tet operator sequence(s) is useful for coordinating the expression of the two nucleotide sequences of interest. Preferably, at least one of the nucleotide sequences to be transcribed is a eukaryotic nucleotide sequence. In one application, the vector is used to produce stoichiometric amounts of two subunits of a heterodimeric molecule in the same cell. For example, the vector can be used produce antibody heavy and light chains in the same cell or to produce growth factor receptor subunits in the same cells. In another application, the vector is used to express two gene products that cooperate in establishing a particular cellular phenotype. In yet another application, the vector is used to coexpress an indicator function and a gene of interest, wherein the indicator is utilized to monitor expression of the gene of interest. Thus, one of the two coordinately expressed sequences can encode a gene of interest and the other can encode a detectable marker, such as a surface marker or enzyme (e.g., β-galactosidase or luciferase) which is used for selection of cells expressing the gene of interest.

Transcription of the two coordinately-regulated nucleotide sequences can be induced by tetracycline (or an analogue thereof) by use of the Tc-inducible transcriptional activator of the invention to regulate expression of the two nucleotide sequences. Thus, in this system, expression of both nucleotide sequences is "off" in the absence of Tc (or analogue), whereas expression is turned "on" by the presence of Tc (or analogue). Alternatively, the vector for coordinate regulation of two nucleotide sequences can be used in conjunction with other tetracycline-regulated transcription factors known in the art. For example, a transactivator fusion protein of a wild-type Tet repressor fused to a transcriptional activation domain, which activates gene expression in the absence of Tc (or analogue), such as the tTA described in Gossen, M. and Bujard, H. (1992) *Proc. Natl. Acad. Sci. U.S.A.* 89:5547-5551, can also be used in conjunction with this target transcription unit for coordinate regulation.

C. Independent Regulation of: Expression of Multiple Nucleotide Sequences

The invention still further permits independent and opposite regulation of two or more nucleotide sequences to be transcribed. Accordingly, another aspect of the invention pertains to a novel tet-regulated transcription unit for independent regulation of two or more genes. To independently regulate the expression of two nucleotide sequences to be transcribed, one nucleotide sequence is operatively linked to a tet operator sequence(s) of one class type and the other nucleotide sequence is operatively linked to a tet operator sequence(s) of another class type. Accordingly, the invention provides at least one recombinant vector for independent regulation of transcription of two nucleotide sequences. In one embodiment, the vector(s) comprises:

a first nucleotide sequence to be a transcribed operatively linked to at least one tet operator sequence of a first class type; and a second nucleotide sequence to be a transcribed operatively linked to at least one tet operator sequence of a second class type.

(It should be understood that each nucleotide sequence to be transcribed also includes an operatively linked, upstream minimal promoter sequence.) The two independently regulated transcription units can be included on a single vector, or alternatively, on two separate vectors. The recombinant vector(s) containing the nucleotide sequences to be transcribed can be introduced into a host cell or animal as described previously.

In another embodiment, the vector(s) does not include the first and second nucleotide sequence to be transcribed but instead contains cloning sites which allow for the introduction into the vector of nucleotide sequences of interest. Accordingly, in this embodiment, the vector(s) comprises:

a first cloning site for introduction of a first nucleotide sequence to be transcribed operatively linked to at least one tet operator sequence of a first class type; and a second cloning site for introduction of a second nucleotide sequence to be transcribed operatively linked to at least one tet operator sequence of a second class type.

This cloning vector(s) may be in a form that already includes first and second minimal promoters operatively linked, respectively, to the first and second cloning sites. Alternatively, nucleotide sequences to be transcribed which include an operatively linked minimal promoter can be introduced into the cloning vector.

In yet another embodiment, the vector for independent regulation of two nucleotide sequences may contain a first nucleotide to be transcribed, such as that encoding a detectable marker or a suicide gene, operatively linked to at least one tet operator sequence of a first class type and a cloning site for introduction of a second nucleotide sequence of interest such that it is operatively linked to at least one tet operator sequence of a second class type.

It will be appreciated by those skilled in the art that various combinations of classes of tet operator sequences can be used for independent regulation of two nucleotide sequences. For example, the first tet operator sequence(s) can be of the class A type and the second can be of the class B type, or the first tet operator sequence can be of the class B type and the second can be of the class C type, etc. Preferably, one to the two tet operators used is a class B type operator.

Independent transcription of the first and second nucleotide sequences is regulated in a host cell by further introducing into the host cell one or more nucleic acids encoding two different transactivator fusion proteins which bind independently to tet operator sequences of different class types. The first fusion protein comprises a polypeptide which binds to a tet operator sequence in the presence of tetracycline or a tetracycline analogue, operatively linked to a polypeptide which activates transcription in enkaryotic cells (e.g., a transactivator fusion protein of the invention, such as a mutated Tn10-derived Tet repressor linked to a VP16 activation region). The second fusion protein comprises a polypeptide which binds to a tet operator sequence in the absence of tetracycline or a tetracycline analogue, operatively linked to a polypeptide which activates transcription in enkaryotic cells (e.g., a wild-type Tn10-derived Tet repressor linked to a VP16 activation region, such as the tTA described in Gossen, M. and Bujard, H. (1992) *Proc. Natl. Acad. Sci. U.S.A.* 89:5547-5551). In one embodiment, the first fusion protein binds to the tet operator sequence of the first class type used in the transcription unit and the second fusion protein binds to the tet operator sequence of the second class type used in the transcription unit. Alternatively, in another embodiment, the first fusion protein binds to the second class type of tet operator and the second fusion protein binds to the first class type of tet operator.

For example, the first nucleotide sequence to be transcribed may be linked to a class A tet operator and the first fusion protein may bind to class A operators, whereas the second nucleotide sequence to be transcribed may be linked to a class B tet operator and the second fusion protein may bind to class B operators. Thus, in this embodiment, transcription of the first nucleotide sequence is activated in the presence of Tc (or analogue thereof) while transcription of the second nucleotide sequence is activated in the absence of Tc (or analogue thereof). Alternatively, in another embodiment, the first fusion protein binds to class B operators and the second fusion protein binds to class A operators. In this case, transcription of the second nucleotide sequence is activated in the presence of Tc (or analogue thereof) while transcription of the first nucleotide sequence is activated in the absence of Tc (or analogue thereof). Appropriate transactivator proteins for use in this system can be designed as described above in Section I and in Gossen and Bujard (1992) cited supra. In order to inhibit heterodimerization between the two different types of Tet repressor fusion proteins present in the same cell, it may be necessary to mutate the dimerization region of one or both of the transactivator fusion proteins. Mutations can be targeted to the C-terminal region of TetR known to be involved in dimerization. The dimerization region has been described in detail based upon the crystal structure of TetR (see Hinrichs, W. et al. (1994) *Science* 264:418-420).

This system allows for independent and opposite regulation of the expression of two genes by Tc and analogues thereof. Use of different Tc analogues as inducing agents may further allow for high, low or intermediate levels of expression of the different sequences (discussed in greater detail in Section V below). The novel transcription unit of the invention for independently regulating the expression of two genes, described above, can be used in situations where two gene products are to be expressed in the same cell but where it is desirable to express one gene product while expression of the other gene product is turned "off", and vice versa. For example, this system is particularly useful for expressing in the same host cell either a therapeutic gene or a suicide gene (i.e., a gene which encodes a product that can be used to destroy the cell, such as ricin or herpes simplex virus thymidine kinase). In many gene therapy situations, it is desirable to be able to express a gene for therapeutic purposes in a host cell but also to have the capacity to destroy the host cell once the therapy is completed. This can be accomplished using the above-described system by linking the therapeutic gene to one class of tet operator and the suicide gene to another class of tet operator. Thus, expression of the therapeutic gene in a host cell can be stimulated by Tc (in which case expression of the suicide gene is absent). Then, once the therapy is complete, Tc is removed, which rams off expression of the therapeutic gene and rams on expression of the suicide gene in the cell.

D. Combined Coordinate and Independent Regulation of Multiple Nucleotide Sequences It is further possible to regulate the expression of four nucleotide sequences by combining the system described in Section IIIB with the system described in Section IIIC such that two pairs of sequences are coordinately regulated while one pair is independently regulated from the other pair. Accordingly, two target transcription units can be designed comprising:

a first nucleic acid comprising in a 5' to 3' direction: a first nucleotide sequence to be transcribed, a tet operator sequence(s) of a first class type, and a second nucleotide sequence to be transcribed a second nucleic acid comprising in a 5' to 3' direction: a third nucleotide sequence to be transcribed, a tet operator sequence(s) of a second class type, and a fourth nucleotide sequence to be transcribed.

Transcription of the first and second nucleotide sequences in the first nucleic acid proceeds in a divergent manner from the first class of tet operator sequence(s). Likewise, transcription of the third and fourth nucleotide sequences in the second nucleic acid proceeds in a divergent manner from the second class of tet operator sequence(s). Thus, expression of the first and second nucleotide sequences is coordinately regulated and expression of the third and fourth nucleotide sequences is coordinately regulated. However, expression of the first and second sequences is independently (and oppositely) regulated compared to the third and fourth sequences through the use of two different transactivator fusion proteins, as described above, one which activates transcription in the presence of Tc (or analogue thereof) and the other which activates transcription in the absence of Tc (or analogue thereof). One transactivator is designed to bind to a tet operators of the first class type and the other is designed to bind to a tet operators of the second class type. In other embodiments, rather than already containing first, second, third and/or fourth nucleotide sequences to be transcribed, these transcription units can contain cloning sites which allow for the introduction of first, second, third and/or fourth nucleotide sequences to be transcribed.

IV. Kits of the Invention

Another aspect of the invention pertains to kits which include the components of the inducible regulatory system of the invention. Such a kit can be used to regulate the expression of a gene of interest (i.e., a nucleotide sequence of interest to be transcribed) which can be cloned into a target transcription unit. In one embodiment, the kit includes a carrier means having in close confinement therein at least two container means: a first container means which contains a first nucleic acid (e.g., DNA) encoding a transactivator fusion protein of the invention (e.g., a recombinant expression vector encoding a first polypeptide which binds to a tet operator sequence in the presence of tetracycline operatively linked to a second polypeptide which activates transcription in enkaryotic cells), and a second container means which contains a second target nucleic acid (e.g., DNA) for the transactivator into which a nucleotide sequence of interest can be cloned. The second nucleic acid typically comprises a cloning site for introduction of a nucleotide sequence to be transcribed (optionally including an operatively linked minimal promoter sequence) and at least one operatively linked tet operator sequence. The term "cloning site" is intended to encompass at least one restriction endonuclease site. Typically, multiple different restriction endonuclease sites (e.g., a polylinker) are contained within the nucleic acid.

To regulate expression of a nucleotide sequence of interest using the components of the kit, the nucleotide sequence is cloned into the cloning site of the target vector of the kit by conventional recombinant DNA techniques and then the first and second nucleic acids are introduced into a host cell or animal. The transactivator fusion protein expressed in the host cell or animal then regulates transcription of the nucleotide sequence of interest in the presence of the inducing agent (Tc or analogue thereof).

Alternatively, in another embodiment, the kit includes a eukaryotic cell which is stably transletted with a nucleic acid encoding a transactivator fusion protein of the invention such that the transactivator is expressed in the cell. Thus, rather than containing nucleic acid alone, the first container means described above can contain a eukaryotic cell line into which the first nucleic acid encoding the transactivator has been stably introduced (e.g., by stable transfection by a conventional method such as calcium phosphate precipitation or electroporation, etc.). In this embodiment, a nucleotide sequence of interest is cloned into the cloning site of the target vector of the kit and then the target vector is introduced into the enkaryotic cell expressing the transactivator fusion protein.

Alternatively or additionally, a recombinant vector of the invention for coordinate regulation of expression of two nucleotide sequences can also be incorporated into a kit of the invention. The vector can be included in the kit in a form that allows for introduction into the vector of two nucleotide sequences of interest. Thus, in another embodiment, a kit of the invention includes 1) a first nucleic acid encoding a transactivator fusion protein of the invention (or a eukaryotic cell into which the nucleic acid has been stably introduced) and 2) a second nucleic acid comprising a nucleotide sequence comprising in a 5' to 3' direction: a first cloning site for introduction of a first nucleotide sequence of interest operatively linked to at least one tet operator sequence operatively linked to a second cloning site for introduction of a second nucleotide sequence of interest, wherein transcription of the first and second nucleotide sequences proceeds in opposite directions from the at least one tet operator sequence. Optionally, the vector can include operatively linked minimal promoter sequences. In another embodiment, the vector can be in a form that already contains one nucleotide sequence to be transcribed (e.g., encoding a detectable marker such as luciferase, β-galactosidase or CAT) and a cloning site for introduction of a second nucleotide sequence of interest to be transcribed.

The transcription units and transactivators of the invention for independent regulation of expression of two nucleotide sequences to be transcribed can also be incorporated into a kit of the invention. The target transcription units can be in a form which allows for introduction into the transcription units of nucleotide sequences of interest to be transcribed. Thus, in another embodiment, a kit of the invention includes 1) a first nucleic acid encoding a transactivator which binds to a tet operator of a first class type in the presence of Tc or an analogue thereof, 2) a second nucleic acid comprising a first cloning site for introduction of a first nucleotide sequence to be transcribed operatively linked to at least one tet operator of a first class type, 3) a third nucleic acid encoding a transactivator which binds to a tet operator of a second class type in the absence of Tc or an analogue thereof, and 4) a fourth nucleic acid comprising a second cloning site for introduction of a second nucleotide sequence to be transcribed operatively linked to at least one tet operator of a second class type. (Optionally, minimal promoter sequences are included in the second and fourth nucleic acids). In another embodiment, one nucleotide sequence to be transcribed (e.g., encoding a suicide gene) is already contained in either the second or the fourth nucleic acid. In yet another embodiment, the nucleic acids encoding the transactivators (e.g., the first and third nucleic acids described above) can be stably introduced into a enkaryotic cell line which is provided in the kit.

In another embodiment, a kit of the invention may include at least one tetracycline or tetracycline analogue. For example, the kit may include a container means which contains tetracycline, anhydrotetracycline, doxycycline, epi-oxytetracycline or other tetracycline analogue described herein.

V. Induction of Gene Expression by Tetracycline or Analogues Thereof

In a host cell which carries both nucleic acid components of the expression system of the invention (as described above), transcription of the nucleotide sequence operatively linked to the tet operator sequence(s) does not occur in the absence of the inducing agent, tetracycline or analogues thereof. Thus, basal transcription of the nucleotide sequence is low or undetectable in the absence of Tc. In order to induce transcription in a host cell, the host cell is contacted with tetracycline or a tetracycline analogue. Accordingly, another aspect of the invention pertains to methods for stimulating transcription of a nucleotide sequence operatively linked to a tet operator sequence in a host cell or animal which expresses a transactivator fusion protein of the invention. The methods involve contacting the cell with tetracycline or a tetracycline analogue or administering tetracycline or a tetracycline analogue to a subject containing the cell.

The term "tetracycline analogue" is intended to include compounds which are structurally related to tetracycline and which bind to the Tet repressor with a $K_a$ of at least about $10^6$ $M^{-1}$. Preferably, the tetracycline analogue binds with an affinity of about $10^9$ $M^{-1}$ or greater. Examples of such tetracycline analogues include, but are not limited to, anhydrotetracycline, doxycycline, chlorotetracycline, oxytetracycline and others disclosed by Hlavka and Boothe, "The Tetracyclines," in *Handbook of Experimental Pharmacology* 78, R. K. Blackwood et al. (eds.), Springer-Verlag, Berlin-New York, 1985; L. A. Mitscher, "The Chemistry of the Tetracycline Antibiotics", *Medicinal Research* 9, Dekker, New York, 1978; Noyee Development Corporation, "Tetracycline Manufacturing Processes" *Chemical Process Reviews*, Park Ridge, N.J. 2 volumes, 1969; R. C. Evans, "The Technology of the Tetracyclines", *Biochemical Reference Series* 1, Quadrangle Press, New York, 1968; and H. F. Dowling, "Tetracycline", *Antibiotic Monographs*, no. 3, Medical Encyclopedia, New York, 1955. Preferred Tc analogues for high level stimulation of transcription are anhydrotetracycline and doxycycline. A Tc analogue can be chosen which has reduced antibiotic activity compared to To. Examples of such Tc analogues are anhydrotetracycline and epioxytetracycline.

To induce gene expression in a cell in vitro, the cell is contacted with Tc or a Tc analogue by culturing the cell in a medium containing the compound. When culturing cells in vitro in the presence of Tc or Tc analogue, a preferred concentration range for the inducing agent is between about 10 and about 1000 ng/ml. Tc or a Tc analogue can be directly added to media in which cells are already being cultured, or more preferably for high levels of gene induction, cells are harvested from Tc-free media and cultured in fresh media containing Tc, or an analogue thereof.

To induce gene expression in vivo, cells within in a subject are contacted with Tc or a Tc analogue by administering the compound to the subject. The term "subject" is intended to include humans and other non-human mammals including monkeys, cows, goats, sheep, dogs, cats, rabbits, rats, mice, and transgenic and homologous recombinant species thereof. Furthermore, the term "subject" is intended to include plants, such as transgenic plants. When the inducing agent is administered to a human or animal subject, the dosage is adjusted to preferably achieve a serum concentration between about 0.05 and 1.0 µg/ml. Tc or a Tc analogue can be administered to a subject by any means effective for achieving an in vivo concentration sufficient for gene induction. Examples of suitable modes of administration include oral administration (e.g., dissolving the inducing agent in the drinking water), slow release pellets and implantation of a diffusion pump. To administer Tc or a Tc analogue to a transgenic plant, the inducing agent can be dissolved in water administered to the plant.

The ability to use different Tc analogues as inducing agents in this system allows for modulate the level of expression of a tet operator-linked nucleotide sequence. As demonstrated in Example 2, anhydrotetracycline and doxycycline have been found to be strong inducing agents. The increase in transcription of the target sequence is typically as high as 1000- to 2000-fold, and induction factors as high as 20,000-fold can be achieved. Tetracycline, chlorotetracycline and oxytetracycline have been found to be weaker inducing agents, i.e., the increase in transcription of a target sequence is in the range of about 10-fold. Thus, an appropriate tetracycline analogue is chosen as an inducing agent based upon the desired level of induction of gene expression. It is also possible to change the level of gene expression in a host cell or animal over time by changing the Tc analogue used as the inducing agent. For example, there may be situations where it is desirable to have a strong burst of gene expression initially and then have a sustained lower level of gene expression. Accordingly, an analogue which stimulates a high levels of transcription can be used initially as the inducing agent and then the inducing agent can be switched to an analogue which stimulates a lower level of transcription. Moreover, when regulating the expression of multiple nucleotide sequences (e.g., when one sequence is regulated by a one of class tet operator sequence(s) and the other is regulated by another class of tet operator sequence(s), as described above in Section IIIC), it may be possible to independently vary the level of expression of each sequence depending upon which transactivator fusion protein is used to regulate transcription and which Tc analogue(s) is used as the inducing agent. Different transactivator fusion proteins are likely to exhibit different levels of responsiveness to Tc analogues. The level of induction of gene expression by a particular combination of transactivator fusion protein and inducing agent (Tc or Tc analogue) can be determined by techniques described herein, (e.g., see Example 2). Additionally, the level of gene expression can be modulated by varying the concentration of the inducing agent. Thus, the expression system of the invention provides a mechanism not only for turning gene expression on or off, but also for "fine tuning" the level of gene expression at intermediate levels depending upon the type and concentration of inducing agent used.

VI. Applications of the Invention

The invention is widely applicable to a variety of situations where it is desirable to be able to turn gene expression on and off, or regulate the level of gene expression, in a rapid, efficient and controlled manner without causing pleiotropic effects or cytotoxicity. Thus, the system of the invention has widespread applicability to the study of cellular development and differentiation in eukaryotic cells, plants and animals. For example, expression of oncogenes can be regulated in a controlled manner in cells to study their function. Additionally, the system can be used to regulate the expression of site-specific recombinases, such as CRE or FLP, to thereby allow for irreversible modification of the genotype of a transgenic organism under controlled conditions at a particular stage of development. For example, drug resistance markers inserted into the genome of transgenic plants that allow for selection of a particular transgenic plant could be irreversibly removed via a Tc-regulated site specific recombinase. Other applications of the regulatory system of the invention include:

A. Gene Therapy

The invention may be particularly useful for gene therapy purposes, in treatments for either genetic or acquired diseases. The general approach of gene therapy involves the introduction of nucleic acid into cells such that one or more gene products encoded by the introduced genetic material are produced in the cells to restore or enhance a functional activity. For reviews on gene therapy approaches see Anderson, W. F. (1992) *Science* 256:808–813; Miller, A. D. (1992) *Nature* 357:455–460; Friedmann, T. (1989) *Science* 244:1275–1281; and Cournoyer, D., et al. (1990) *Curr. Opin. Biotech.* 1:196–208. However, current gene therapy vectors typically utilize constitutive regulatory elements which are responsive to endogenous transcriptions factors. These vector systems do not allow for the ability to modulate the level of gene expression in a subject. In contrast, the inducible regulatory system of the invention provides this ability.

To use the system of the invention for gene therapy purposes, cells of a subject in need of gene therapy are modified to contain 1) nucleic acid encoding a transactivator fusion protein of the invention in a form suitable for expression of the transactivator in the host cells and 2) a gene of interest (e.g., for therapeutic purposes) operatively linked to a tet operator sequence(s). The cells of the subject can be modified ex vivo and then introduced into the subject or the cells can be directly modified in vivo (methods for modification of the cells are described above in Section II). Expression of the gene of interest in the cells of the subject is then stimulated by administering Tc or a Tc analogue to the patient. The level of gene expression can be varied depending upon which particular Tc analogue is used as the inducing agent. The level of gene expression can also be modulated by adjusting the dose of the tetracycline, or analogue thereof, administered to the patient to thereby adjust the concentration achieved in the circulation and the tissues of interest. Conventional detection methods known in the art, such as an enzyme linked immunosorbent assay, can be used to monitor the expression of the regulated protein of interest and the concentration of Tc or Tc analogue can be varied until the desired level of expression of the protein of interest is achieved. Accordingly, expression of a protein of interest can be adjusted according to the medical needs of an individual, which may vary throughout the lifetime of the individual. To stop expression of the gene of interest in cells of the subject, administration of the inducing agent is stopped. Thus, the regulatory system of the invention offers the advantage over constitutive regulatory systems of allowing for modulation of the level of gene expression depending upon the requirements of the therapeutic situation.

Genes of particular interest to be expressed in cells of a subject for treatment of genetic or acquired diseases include those encoding adenosine deaminase, Factor VIII, Factor IX, dystrophin, β-globin, LDL receptor, CFTR, insulin, erythropoietin, anti-angiogenesis factors, growth hormone, glucocerebrosidase, β-glucouronidase, α1-antitrypsin, phenylalanine hydroxylase, tyrosine hydroxylase, ornithine transcarbamylase, arginosuccinate synthetase, UDP-glucuronysyl transferase, apoA1, TNF, soluble TNF receptor, interleukins (e.g., IL-2), interferons (e.g., α-or γ-IFN) and other cytokines and growth factors. Cells types which can be modified for gene therapy purposes include hematopoietic stem cells, myoblasts, hepatocytes, lymphocytes, skin epithelium and airway epithelium. For further descriptions of cell types, genes and methods for gene therapy see e.g., Wilson, J. M et al. (1988) *Proc. Natl. Acad. Sci. U.S.A.* 85:3014–3018; Armentano, D. et al. (1990) *Proc. Natl. Acad. Sci. U.S.A.* 87:6141–6145; Wolff, J. A. et al. (1990) *Science* 247:1465–1468; Chowdhury, J. R. et al. (1991) *Science* 254:1802–1805; Ferry, N. et al. (1991) *Proc. Natl. Acad. Sci. U.S.A.* 88:8377–8381; Wilson, J. M. et al. (1992) *J. Biol. Chem.* 267:963–967; Quantin, B. et al. (1992) *Proc. Natl. Acad. Sci. U.S.A.* 89:2581–2584; Dai, Y. et al. (1992) *Proc. Natl. Acad. Sci. U.S.A.* 89:10892–10895; van Beusechem, V. W. et al. (1992) *Proc. Natl. Acad. Sci. U.S.A.* 89:7640–7644; Rosenfeld, M. A. et al. (1992) *Cell* 68:143–155; Kay, M. A. et al. (1992) *Human Gene Therapy* 3:641–647; Cristiano, R. J. et al. (1993) *Proc. Natl. Acad. Sci. U.S.A.* 90:2122–2126; Hwu, P. et al. (1993) *J. Immunol.* 150:4104–4115; and Herz, J. and Gerard, R. D. (1993) *Proc. Natl. Acad. Sci. U.S.A.* 90:2812–2816.

Gene therapy applications of particular interest in cancer treatment include overexpression of a cytokine gene (e.g., TNF-α) in tumor infiltrating lymphocytes or ectopic expression of cytokines in tumor cells to induce an anti-tumor immune response at the tumor site), expression of an enzyme in tumor cells which can convert a non-toxic agent into a toxic agent, expression of tumor specific antigens to induce an anti-tumor immune response, expression of tumor suppressor genes (e.g., p53 or Rb) in tumor cells, expression of a multidrug resistance gene (e.g., MDR1 and/or MRP) in bone marrow cells to protect them from the toxicity of chemotherapy.

Gene therapy applications of particular interest in treatment of viral diseases include expression of trans-dominant negative viral transactivation proteins, such as trans-dominant negative tat and rev mutants for HIV or trans-dominant ICp4 mutants for HSV (see e.g., Balboni, P. G. et al. (1993) *J. Med. Virol.* 41:289–295; Liem, S. E. et al. (1993) *Hum. Gene Ther.* 4:625–634; Malim, M. H. et al. (1992) *J. Exp. Med.* 76:1197–1201; Daly, T. J. et al. (1993) *Biochemistry* 32:8945–8954; and Smith, C. A. et al. (1992) *Virology* 191:581–588), expression of trans-dominant negative envelope proteins, such as env mutants for HIV (see e.g., Steffy, K. R. et al. (1993) *J. Virol.* 67:1854–1859), intracellular expression of antibodies, or fragments thereof, directed to viral products ("internal immunization", see e.g., Marasco, W. A. et al. (1993) *Proc. Natl. Acad. Sci. U.S.A.* 90:7889–7893) and expression of soluble viral receptors, such as soluble CD4. Additionally, the system of the invention can be used to conditionally express a suicide gene in cells, thereby allowing for elimination of the cells after they have served an intended function. For example, cells used for vaccination can be eliminated in a subject after an immune response has been generated the subject by inducing expression of a suicide gene in the cells by administering Tc or a Tc analogue to the subject.

B. Production of Proteins in Vitro

Large scale production of a protein of interest can be accomplished using cultured cells in vitro which have been modified to contain 1) a nucleic acid encoding a transactivator fusion protein of the invention in a form suitable for expression of the transactivator in the cells and 2) a gene encoding the protein of interest operatively linked to a tet operator sequence(s). For example, mammalian, yeast or fungal cells can be modified to contain these nucleic acid components as described herein. The modified mammalian, yeast or fungal cells can then be cultured by standard fermentation techniques in the presence of Tc or an analogue thereof to induce expression of the gene and produce the protein of interest. Accordingly, the invention provides a production process for isolating a protein of interest. In the process, a host cell (e.g., a yeast or fungus), into which has been introduced both a nucleic acid encoding a transactivator fusion protein of the invention and a nucleic acid encoding the protein, of the interest operatively linked to at least one tet operator sequence, is grown at production scale in a culture medium in the presence of tetracycline or a tetracycline analogue to stimulate transcription of the nucleotides sequence encoding the protein of interest (i.e., the nucleotide sequence operatively linked to the tet operator sequence(s)) and the protein of interest is isolated from harvested host cells or from the culture medium. Standard protein purification techniques can be used to isolate the protein of interest from the medium or from the harvested cells.

C. Production of Proteins in Vivo

The invention also provides for large scale production of a protein of interest in animals, such as in transgenic farm animals. Advances in transgenic technology have made it possible to produce transgenic livestock, such as cattle, goats, pigs and sheep (reviewed in Wall, R. J. et al. (1992) *J. Cell. Biochem.* 49:113–120; and Clark, A. J. et al. (1987) *Trends in Biotechnology* 5:20–24). Accordingly, transgenic livestock carrying in their genome the components of the inducible regulatory system of the invention can be constructed, wherein a gene encoding a protein of interest is operatively linked to at least one tet operator sequence. Gene expression, and thus protein production, is induced by administering Tc (or analogue thereof) to the transgenic animal. Protein production can be targeted to a particular tissue by linking the nucleic acid encoding the transactivator fusion protein to an appropriate tissue-specific regulatory element(s) which limits expression of the transactivator to certain cells. For example, a mammary gland-specific regulatory element, such as the milk whey promoter (U.S. Pat. No. 4,873,316 and European Application Publication No. 264,166), can be linked to the transactivator transgene to limit expression of the transactivator to mammary tissue. Thus, in the presence of Tc (or analogue), the protein of interest will be produced in the mammary tissue of the transgenic animal. The protein can be designed to be secreted into the milk of the transgenic animal, and if desired, the protein can then be isolated from the milk.

Advantages

The inducible regulatory system of the invention addresses and overcomes many of the limitations of other inducible regulatory systems in the art. For example, very high intracellular concentrations of the transcriptional activator fusion protein of the invention are not required for efficient regulation of gene expression. Additionally, since gene expression is induced by adding rather than removing the inducing agent, the induction kinetics in the system of the invention are not limited by the rate of removal of the inducing agent and thus are typically faster. Moreover, the inducing agent is only present when gene transcription is induced, thereby avoiding the need for the continuous presence of an agent to keep gene expression off.

Furthermore, in contrast to various versions of the lac system (e.g., Labow et al. (1990) *Mol. Cell. Biol.* 10:3343–3356; Baim et al. (1991) *Proc. Natl. Acad. Sci. U.S.A.* 88:5072–5076), which are limited by the negative properties of the inducing agent (IPTG) and/or by the need to increase the temperature in order to induce gene expression (which may elicit pleiotropic effects), the inducing agent used in the system of the invention (Tc or an analogue thereof) has many advantageous properties: 1) Tc and analogues thereof exhibit high affinity for TetR and low toxicity for eukaryotic cells, and thus can be used for gene induction at concentrations that do not affect cell growth or morphology; 2) Tc analogues which retain TetR binding but which have reduced antibiotic activity exist and can be used as inducing agents, thereby avoiding possible side effects from the antibiotic property of Tc; 3) the pharmacokinetic properties of Tc and T analogues enable rapid and efficient cellular uptake and penetration of physiological barriers, such as the placenta or the blood-brain barrier; and 4) Tc analogues with different induction capabilities permit modulation of the level of gene expression.

Thus, the invention provides an inducible regulatory system which allows for rapid activation of gene transcription without cellular toxicity and a range of induction indices. The increase in gene expression upon induction typically is between 1000- and 2000-fold and can be as high as about 20,000-fold. Alternatively, lower levels of gene induction, e.g., 10-fold, can be achieved depending upon which inducing agent is used. This system can be utilized in a wide range of applications. These applications include gene therapy, large-scale production of proteins in cultured cells or in transgenic farm animals, and the study of gene function, for example in relationship to cellular development and differentiation. Moreover, the novel transcription units of the invention allow for coordinate or independent regulation of the expression of multiple genes utilizing the regulatory components of the invention.

This invention is further illustrated by the following examples which should not be construed as limiting. The contents of all references, patents and published patent applications cited throughout this application are hereby incorporated by reference.

EXAMPLE 1

Selection of a Mutated Tet Repressor and Construction of a Tetracycline Inducible Transcriptional Activator A "reverse" Tet repressor, which binds to its target DNA in the presence rather than the absence of tetracycline, was generated by chemical mutagenesis and selection essentially as described in Hecht, B. et al. (1993) *J. Bacteriology* 175:1206–1210. Single-stranded DNA (coding and noncoding strands) encoding the wild-type Tn10-derived Tet repressor was chemically mutagenized with sodium nitrite. Single-stranded DNAs (40 μg in 40 μl in Tris-EDTA buffer) were mixed with 10 μl of 2.5M sodium acetate (pH 4.3) and 50 μl of sodium nitrate ranging between 0.25M and 2M and incubated for 45 to 60 minutes at room temperature. After mutagenesis, the complementary strand was synthesized using reverse transcriptase or by amplification using the polymerase chain reaction with Taq DNA polymerase. Since the mutagenesis procedure yields multiple mutations in the DNA, three fragments of the gene, of about 200 base pairs each, were individually subcloned into a wt Tet repressor gene in a recombinant expression vector to replace the corresponding portion of the wild-type gene. This created a pool of mutated Tet repressor genes wherein each gene had mostly single mutations in the 200 base pair mutagenized fragment of the gene.

The pool of mutated Tet repressors were screened in a genetic assay which positively selects for a functional interaction between a Tet repressor and its cognate operator using *E. coli.* strain WH207(λWH25) (the construction of this strain is described in detail in Wissmann, A. et al. (1991) *Genetics* 128:225–232). In this *E. coli* strain, tet operators direct the expression of divergently arranged β-galactoside (lacZ) and Lac repressor (lacI) genes and the lac regulatory region directs the expression of a galactokinase (galK) gene. Binding of Tet repressors to tet operators rams off transcription of the lacI and lacZ genes. The absence of Lac repressor allows for expression of the galK gene, which enables the *E. coli* strain to use galaclose as a sole carbon source, which serves as one marker. The lacZ⁻ phenotype serves as a second marker. Thus, bacteria containing Tet repressors which bind to tet operators have a Gal⁺, lacZ⁻ phenotype. Bacteria containing wild-type Tet repressors have a Gal⁺, lacZ⁻ phenotype in the absence of tetracycline. A mutated "reverse" Tet repressor (rTetR) was selected based upon a Gal⁺, lacZ⁻ phenotype in the presence of tetracycline.

The nucleotide and amino acid sequence of the rTetR mutant are shown in SEQ ID NOs: 1 (nucleotide positions 1–621) and 2 (amino acid positions 1–207), respectively. Sequence analysis of the rTetR mutant showed the following amino acid and nucleotide changes:

| aa (position) | | affected codon | |
| --- | --- | --- | --- |
| wild-type | mutant | wild type | mutant |
| glu (71) | lys | GAA | AAA |
| asp (95) | asn | GAT | AAT |
| leu (101) | ser | TTA | TCA |
| gly (102) | asp | GGT | GAT |

Two additional mutations did not result in an amino acid exchange:

| aa (position) | | affected codon | |
| --- | --- | --- | --- |
| wild-type | mutant | wild type | mutant |
| leu (41) | leu | TTG | CTG |
| arg (80) | arg | CGT | CGC |

To convert the rTetR mutant to a transcriptional activator, a 399 base pair XbaI/Eco47III fragment encoding amino acids 3 to 135 of rTetR (i.e., encompassing the mutated region) was exchanged for the corresponding restriction fragment of the expression vector pUHD15-1 to create pUHD17-1. In pUHD15-1, nucleotide sequences encoding wild-type TetR are linked in frame to nucleotide sequences encoding the C-terminal 130 amino acids of herpes simplex virus VP16. These transactivator sequences are flanked upstream by a CMV promoter/enhancer and downstream by an SV40 poly(A) site (the construction of pUHD15-1 is described in more detail in U.S. Ser. No. 08/076,726 and Gossen, M. and Bujard, H. (1992) Proc. Natl. Acad. Sci. U.S.A. 89:5547–5551). Thus, in pUHD17-1, nucleotide sequences encoding the reverse TetR mutant are linked in frame to VP 16 sequences to create a reverse Tc-controlled transactivator (referred to herein as $tTA^R$). The analogous exchange of the mutated region of rTetR for the wild-type region of TetR was performed with plasmid pUHD152-1, which is the same as pUHD15-1 except that it additionally contains nucleotide sequences encoding a nuclear localization signal linked in-frame to the 5' end of the nucleotide sequences encoding the Tet repressor. The amino acid sequence of the nuclear localization signal is MPKRPRP (SEQ ID NO: 5), which is linked to the serine at amino acid position 2 of TetR. The resulting expression vector encoding the reverse Tc-controlled transactivator including a nuclear localization signal (referred to herein as $ntTA^R$) was named pUHD172-1.

EXAMPLE 2

Tetracycline-Induced Stimulation of Transcription by $tTA^R$

Transient Transfection

The pUHD17-1 and pUHD172-1 expression vectors were transiently transfected by a standard calcium phosphate method into HeLa cells together with a reporter plasmid, pUHC13-3, in which heptameric tet operators are fused upstream of a minimal hCMV-promoter and a luciferase reporter gene (the reporter plasmid is described in detail in U.S. Ser. No. 08/076,726 and Gossen, M. and Bujard, H. (1992) Proc. Natl. Acad. Sci. U.S.A. 89:5547–5551) After incubation of the transfected cells at 37° C. for 20 hours in the presence or absence of tetracycline (or an analogue thereof), luciferase activity was assayed as follows: Cells grown to ~80% confluency in 35 mm dishes in Eagle's minimal essential medium were washed with 2 ml of phosphate-buffered saline before they were lysed in 25 mM Tris phosphate, pH 7.8/2 mM dithiothreitol/2 mM diaminocyclohexanetetraacetic acid/10% glycerol/1% Triton-X-100 for 10 minutes at room temperature. The lysate was scraped off the culture dishes and centrifuged for 10 seconds in an Eppendorf centrifuge. Next, aliquots (10 µl) of the supernatant were mixed with 250 µl of 25 mM glycylglycine/15 mM MgSO4/5 mM ATP and assayed for luciferase activity in a Lumat LB9501 (Berthold, Wildbad, F. R. G.) using the integral mode (10 seconds). D-Luciferin (L6882, Sigma) was used at 0.5 mM. The background signal measured in extracts of HeLa cells that did not contain a luciferase gene was indistinguishable from the instrument background (80–120 relative light units (rlu)/10 sec.). Protein content of the lysate was determined according to Bradford (Bradford, M. M. (1976) Anal. Biochem. 72:248–254). Cells transfected with plasmids encoding either $tTA^R$ or $ntTA^R$ showed an increased level of luciferase activity in the presence of tetracyclines. This effect was consistently more pronounced when anhydrotetracycline (ATe) was used instead of tetracycline.

Stable Transfection

After this transient transfection analysis, expression vectors were prepared for stable transfection of cells. A pSV2neo-derived neomycin resistance cassette (described in Southern, P. J. and Berg, P. (1982) J. Mol. Appl. Genet. 1:327–341) was integrated into the transactivator expression vectors pUHD17-1 and pUHD172-1, resulting in pUHD17-1 neo and pUHD172-1 neo, respectively. pUHD172-1 neo, coding for $ntTA^R$, was stably integrated into HeLa cells by standard techniques. Ten G418-resistant cell clones were analyzed for their phenotype by transient supertransfection with pUHC13-3 carrying the luciferase gene under the control of a minimal CMV promoter and tet operators. Three clones, HR4, HR5 and HR10, showed a strong increase of luciferase activity in the presence of ATe. From these clones, HR5 was selected for further experiments.

To create stable transfectants for both $ntTA^R$ and a tet operator-linked luciferase reporter gene, HR5 cells were cotransfected with pUH13-3 and pHMR272, which encodes for hygromycin resistance (see Bernhard, H-U. et al. (1985) Exp. Cell Res. 158:237–243), and hygromycin resistant clones were selected. In an analogous experiment, HR5 cells were cotransfected with pUH13-7 and pHMR272. pUH13-7 contains a minimal promoter sequence spanning position +19 to −37 of the HSVtk promoter adjacent to the heptameric tetO sequences, rather than a minimal CMV promoter. From 21 hygromycin resistant clones, 10 showed inducible luciferase activity upon addition of Tc or doxyciscline (Dc) to the culture medium. Clones containing the luciferase reporter gene linked to a minimal CMV promoter are referred to as HR5-C, whereas those containing the luciferase reporter gene linked to a minimal tk promoter are referred to HR5-T.

Six of the HR5 clones stably transfected with a $ntTA^R$-dependent reporter unit and previously shown to be responsive to tetracyclines were grown in parallel in the absence or presence of 1 µg/ml doxycycline. About $3\times10^4$ cells were plated in each 35 mm dish (4 dishes for each clone). After growth for 60 hours, cells were harvested and the luciferase activity of the extracts (in relative light units (rlu)/µg extracted protein) was determined. As shown in Table 1, the absolute expression levels of six clones demonstrate that activation of luciferase gene expression over 3 orders of magnitude is achieved in several of the double stable cell lines containing the $ntTA^R$ regulatory system.

It should be noted that even higher induction factors (e.g., as high as a 20,000-fold increase in expression) could be achieved if, instead of simply adding the inducing agent to the culture medium, the cells were washed prior to induction and then replated in fresh culture medium containing the inducing agent.

TABLE 1

Doxycycline-dependent luciferase activity of different double stable luc+/HR5 cell clones
Luciferase Activity, rlu/μg protein

| Clone | −Doxycyline | +Doxycycline | Induction Factor |
|---|---|---|---|
| HR5-C6 | 65 | 54,911 | 845 |
|  | 62 | 69,525 | 1120 |
| HR5-C11 | 100 | 165,671 | 1660 |
|  | 142 | 179,651 | 1270 |
| HR5-C14 | 43 | 44,493 | 1030 |
|  | 43 | 56,274 | 1310 |
| HR5-T2 | 56 | 16,696 | 298 |
|  | 40 | 16,416 | 410 |
| HR5-T15 | 6.8 | 1838 | 270 |
|  | 6.5 | 1688 | 260 |
| HR5-T19 | 4.8 | 1135 | 236 |
|  | 5.4 | 1285 | 237 |

Induction of Luciferase Activity by Different Tetracyclines

The ability of tetracycline and several different tetracycline analogues to induce luciferase expression in HR5-C11 cells was examined. HR5-C11 cells plated at a density of about $3 \times 10^4$ cells/35 mm dish (~80% confluency). After full attachment of the cells, the following tetracyclines ere added to the cultures at a concentration of 1 μg/ml: tetracycline-HCl (Tc), oxytetracycline-HCl (OTc), chlorotetracycline (CTc), anhydrotetracycline-HCl (ATc) and doxycycline-HCl (Doxy). These compounds are commercially available from Sigma Chemical Co., St. Louis, Mo., and were kept in aqueous solution at a concentration of 1 μg/ml. Cells grown in the absence of antibiotic (−) served as a control. After 3 days, the cells were harvested and the luciferase activity and the protein content of the extracts were determined. The results are shown in the bar graph of FIG. 1. Each bar in the figure (closed and hatched) represents the relative luciferase activity (normalized toward the amount of extracted protein) of a single culture dish. The mean of the luciferase activities obtained from the two plates grown without tetracyclines was defined as 1. Tc, CTc and OTc showed modest stimulation of luciferase activity. By contrast, ATc and Doxy stimulated luciferase activity approximately 1000 and 1500 fold, respectively.

Dose-response of Luciferase Activity to Doxycycline in HR5-C11 Cells

The above-described experiment examining the induction ability of different tetracyclines revealed that doxycycline was the most potent effector of the tetracyclines examined. Doxycycline was therefore selected to quantitatively analyze its dose-response. HR5-C11 cells were incubated with different concentrations of doxycycline and luciferase activity was measured. The data of three independent experiments are shown in FIG. 2. At less than 10 ng/ml in the culture medium, doxycycline is ineffective at inducing luciferase activity. However, when the concentration was raised above 10 ng/ml, an almost linear increase in expression of luciferase was observed. Maximal activation was achieved at 1 μg/ml. At concentrations above 3 μg/ml, doxycycline showed a slight growth-inhibitory effect on HeLa cells as determined in a MTT-assay.

Kinetics of Induction of the ntTA$^R$ System

Figure 3:
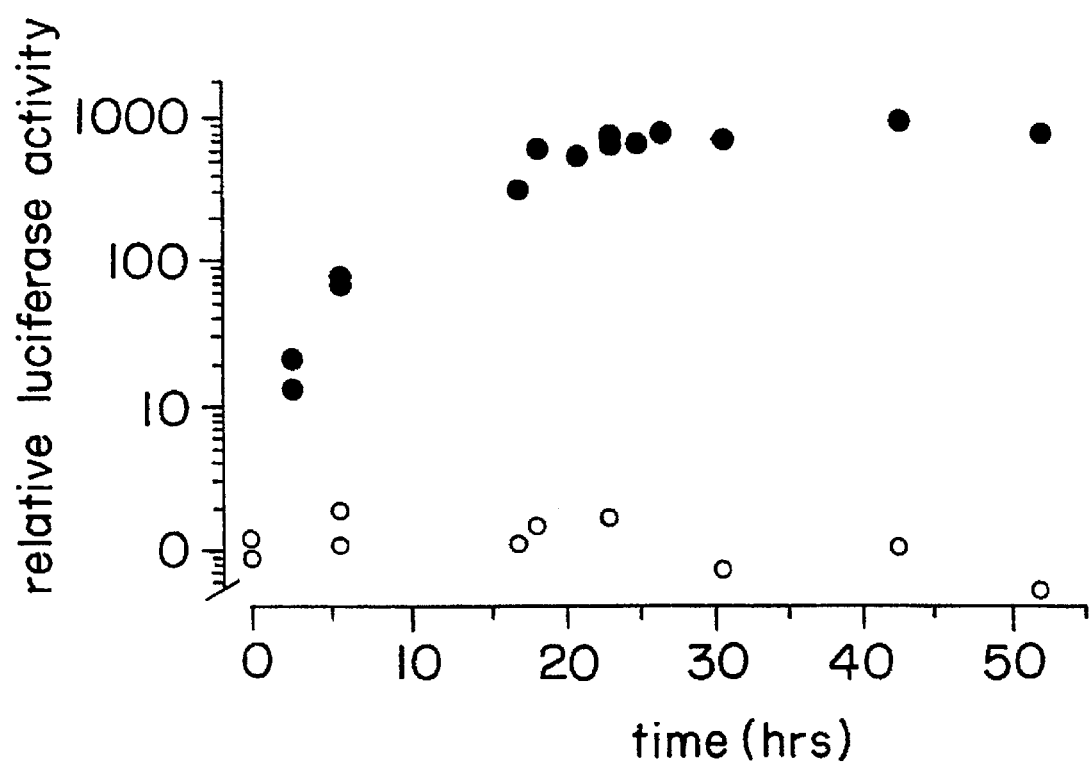
FIG. 3 is a graph depicting the kinetics of induction of luciferase activity in HR5-C 11 cells by doxycycline. HR5-C11 cultures were exposed to 1 μg/ml of doxycycline and luciferase activity was measured after different time intervals; (•) cultures containing doxycycline, (o) cultures grown in the absence of antibiotic.

To examine the kinetics of doxycycline-induced ntTA$^R$ mediated induction of gene expression, the time course of induction of luciferase activity in HR5-C11 cells was monitored after addition of doxycycline to the medium (final concentration 1 μg/ml). Cells were cultured in the presence of doxycycline and after various time intervals, the cells were harvested and luciferase activity was determined as described above. As shown in FIG. 3, a 100-fold induction of luciferase activity was observed after 5.5 hours incubation with Doxy. Fully induced levels were achieved in less than 24 hours of incubation with Doxy. Thus, these results indicate that induction of gene expression occurs rapidly following exposure of the cells to the inducing agent.

EXAMPLE 3

Coordinate Regulation of the Expression of Two Nucleotide Sequences by a Tc-Controlled Transcriptional Activator A recombinant expression vector for coordinate, bidirectional transcription of two nucleotide sequences was constructed comprising, in a 5' to 3' direction: a luciferase gene, a first minimal promoter, seven tet operator sequences, a second minimal promoter and a LacZ gene. The construct is illustrated in FIG. 6. In this construct, the luciferase and LacZ genes are oriented such that they are transcribed in opposite orientations relative to the tet operator sequences, i.e., the luciferase gene is transcribed in a 5' to 3' direction from the bottom strand of DNA, whereas the LacZ gene is transcribed in a 5' to 3' direction from the top strand of DNA. The luciferase gene is followed by an SV40 polyadenylation signal, whereas the LacZ gene is followed by a β-globin polyadenylation signal.

Figure 8A:
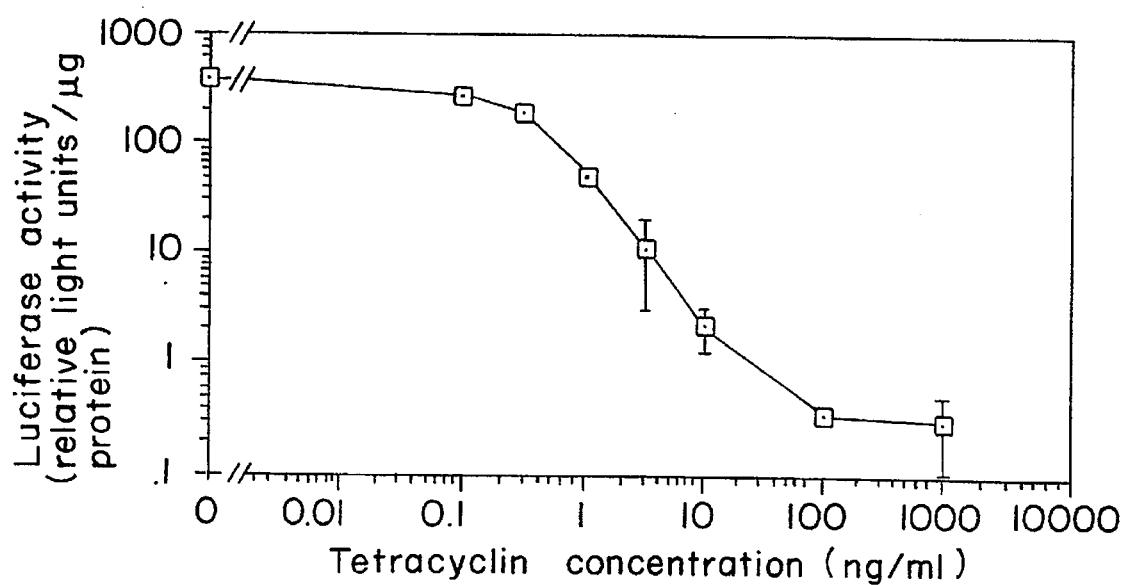
FIGS. 8A–8B are two graphs depicting coordinate expression of luciferase and β-galactosidase activity by a tetracycline-regulated transcriptional activator.
Figure 8B:
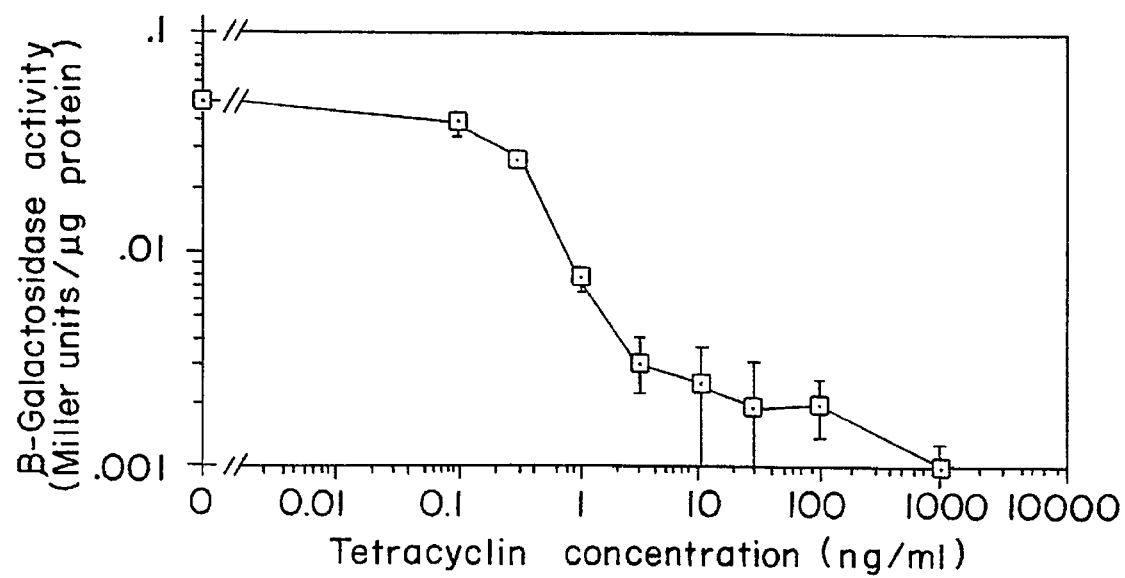

The construct was transfected into the HeLa cell line HtTA-1 cells, which express a wild-type Tet repressor-VP16 fusion protein (referred to as tTA and described in Gossen, M. and Bujard, H. (1992) Proc. Natl. Acad. Sci. U.S.A. 89:5547–5551). The tTA fusion protein binds to tet operator sequences in the absence of Tc (or analogue) but not in the presence of Tc (or analogue). The construct was cotransfected into HtTA-1 cells with a plasmid which confers hygromycin resistance and stably transfected clones were selected based upon their hygromycin resistant phenotype. Selected hygromycin resistant (Hygr$^r$) clones were examined for luciferase and β-galactosidase activity. Clones positive for all three markers (Hygr$^r$, luc$^+$, β-gal$^+$) were then examined for tetracycline-dependent coregulation of expression of luciferase and β-galactosidase activity by culturing the clones in increasing amounts of tetracycline and measuring luciferase and β-galactosidase activity. The results of such an experiment using clone Htl316–8/50 are shown in FIG. 8A–8B. In the absence of tetracycline (in which case tTA can bind to tet operators and activate gene expression), both luciferase and β-galactosidase activity is detected. In the presence of increasing amounts of tetracycline, luciferase and β-galactosidase activity are coordinately and equivalently downregulated. This data demonstrates that expression of two genes can be coordinately regulated by a tetracycline-controlled transactivator by operatively linking the two genes to the same tet operator sequence(s).

EQUIVALENTS

Those skilled in the art will recognize, or be able to ascertain using no more than routine experimentation, many equivalents to the specific embodiments of the invention described herein. Such equivalents are intended to be encompassed by the following claims.

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 1008 base pairs
        ( B ) TYPE: nucleic acid
        ( C ) STRANDEDNESS: double
        ( D ) TOPOLOGY: linear ( i i ) MOLECULE TYPE: DNA ( i x ) FEATURE:
        ( A ) NAME/KEY: exon
        ( B ) LOCATION: 1..1008

( i x ) FEATURE:
        ( A ) NAME/KEY: mRNA
        ( B ) LOCATION: 1..1008

( i x ) FEATURE:
        ( A ) NAME/KEY: misc. binding
        ( B ) LOCATION: 1..207

( i x ) FEATURE:
        ( A ) NAME/KEY: misc. binding
        ( B ) LOCATION: 208..335

( i x ) FEATURE:
        ( A ) NAME/KEY: CDS
        ( B ) LOCATION: 1..1005

( x i ) SEQUENCE DESCRIPTION: SEQ ID NO:1:

```
ATG  TCT  AGA  TTA  GAT  AAA  AGT  AAA  GTG  ATT  AAC  AGC  GCA  TTA  GAG  CTG       48
Met  Ser  Arg  Leu  Asp  Lys  Ser  Lys  Val  Ile  Asn  Ser  Ala  Leu  Glu  Leu
 1              5                        10                       15

CTT  AAT  GAG  GTC  GGA  ATC  GAA  GGT  TTA  ACA  ACC  CGT  AAA  CTC  GCC  CAG       96
Leu  Asn  Glu  Val  Gly  Ile  Glu  Gly  Leu  Thr  Thr  Arg  Lys  Leu  Ala  Gln
         20                       25                       30

AAG  CTA  GGT  GTA  GAG  CAG  CCT  ACA  CTG  TAT  TGG  CAT  GTA  AAA  AAT  AAG      144
Lys  Leu  Gly  Val  Glu  Gln  Pro  Thr  Leu  Tyr  Trp  His  Val  Lys  Asn  Lys
 35                      40                       45

CGG  GCT  TTG  CTC  GAC  GCC  TTA  GCC  ATT  GAG  ATG  TTA  GAT  AGG  CAC  CAT      192
Arg  Ala  Leu  Leu  Asp  Ala  Leu  Ala  Ile  Glu  Met  Leu  Asp  Arg  His  His
         50                       55                       60

ACT  CAC  TTT  TGC  CCT  TTA  AAA  GGG  GAA  AGC  TGG  CAA  GAT  TTT  TTA  CGC      240
Thr  His  Phe  Cys  Pro  Leu  Lys  Gly  Glu  Ser  Trp  Gln  Asp  Phe  Leu  Arg
 65              70                       75                       80

AAT  AAG  GCT  AAA  AGT  TTT  AGA  TGT  GCT  TTA  CTA  AGT  CAT  CGC  AAT  GGA      288
Asn  Lys  Ala  Lys  Ser  Phe  Arg  Cys  Ala  Leu  Leu  Ser  His  Arg  Asn  Gly
 85                      90                       95

GCA  AAA  GTA  CAT  TCA  GAT  ACA  CGG  CCT  ACA  GAA  AAA  CAG  TAT  GAA  ACT      336
Ala  Lys  Val  His  Ser  Asp  Thr  Arg  Pro  Thr  Glu  Lys  Gln  Tyr  Glu  Thr
        100                      105                      110

CTC  GAA  AAT  CAA  TTA  GCC  TTT  TTA  TGC  CAA  CAA  GGT  TTT  TCA  CTA  GAG      384
Leu  Glu  Asn  Gln  Leu  Ala  Phe  Leu  Cys  Gln  Gln  Gly  Phe  Ser  Leu  Glu
115                      120                      125

AAT  GCA  TTA  TAT  GCA  CTC  AGC  GCT  GTG  GGG  CAT  TTT  ACT  TTA  GGT  TGC      432
Asn  Ala  Leu  Tyr  Ala  Leu  Ser  Ala  Val  Gly  His  Phe  Thr  Leu  Gly  Cys
         130                      135                      140

GTA  TTG  GAA  GAT  CAA  GAG  CAT  CAA  GTC  GCT  AAA  GAA  GAA  AGG  GAA  ACA      480
Val  Leu  Glu  Asp  Gln  Glu  His  Gln  Val  Ala  Lys  Glu  Glu  Arg  Glu  Thr
145                      150                      155                      160
```

| | | | | | | | | | | | | | | | | |
|---|---|---|---|---|---|---|---|---|---|---|---|---|---|---|---|---|
| CCT | ACT | ACT | GAT | AGT | ATG | CCG | CCA | TTA | TTA | CGA | CAA | GCT | ATC | GAA | TTA | 528 |
| Pro | Thr | Thr | Asp | Ser | Met | Pro | Pro | Leu | Leu | Arg | Gln | Ala | Ile | Glu | Leu | |
| 165 | | | | | 170 | | | | | 175 | | | | | | |
| TTT | GAT | CAC | CAA | GGT | GCA | GAG | CCA | GCC | TTC | TTA | TTC | GGC | CTT | GAA | TTG | 576 |
| Phe | Asp | His | Gln | Gly | Ala | Glu | Pro | Ala | Phe | Leu | Phe | Gly | Leu | Glu | Leu | |
| | 180 | | | | | 185 | | | | | 190 | | | | | |
| ATC | ATA | TGC | GGA | TTA | GAA | AAA | CAA | CTT | AAA | TGT | GAA | AGT | GGG | TCC | GCG | 624 |
| Ile | Ile | Cys | Gly | Leu | Glu | Lys | Gln | Leu | Lys | Cys | Glu | Ser | Gly | Ser | Ala | |
| 195 | | | | | 200 | | | | | 205 | | | | | | |
| TAC | AGC | CGC | GCG | CGT | ACG | AAA | AAC | AAT | TAC | GGG | TCT | ACC | ATC | GAG | GGC | 672 |
| Tyr | Ser | Arg | Ala | Arg | Thr | Lys | Asn | Asn | Tyr | Gly | Ser | Thr | Ile | Glu | Gly | |
| | 210 | | | | | 215 | | | | | 220 | | | | | |
| CTG | CTC | GAT | CTC | CCG | GAC | GAC | GAC | GCC | CCC | GAA | GAG | GCG | GGG | CTG | GCG | 720 |
| Leu | Leu | Asp | Leu | Pro | Asp | Asp | Asp | Ala | Pro | Glu | Glu | Ala | Gly | Leu | Ala | |
| 225 | | | | | 230 | | | | | 235 | | | | | 240 | |
| GCT | CCG | CGC | CTG | TCC | TTT | CTC | CCC | GCG | GGA | CAC | ACG | CGC | AGA | CTG | TCG | 768 |
| Ala | Pro | Arg | Leu | Ser | Phe | Leu | Pro | Ala | Gly | His | Thr | Arg | Arg | Leu | Ser | |
| 245 | | | | | 250 | | | | | 255 | | | | | | |
| ACG | GCC | CCC | CCG | ACC | GAT | GTC | AGC | CTG | GGG | GAC | GAG | CTC | CAC | TTA | GAC | 816 |
| Thr | Ala | Pro | Pro | Thr | Asp | Val | Ser | Leu | Gly | Asp | Glu | Leu | His | Leu | Asp | |
| | 260 | | | | | 265 | | | | | 270 | | | | | |
| GGC | GAG | GAC | GTG | GCG | ATG | GCG | CAT | GCC | GAC | GCG | CTA | GAC | GAT | TTC | GAT | 864 |
| Gly | Glu | Asp | Val | Ala | Met | Ala | His | Ala | Asp | Ala | Leu | Asp | Asp | Phe | Asp | |
| 275 | | | | | 280 | | | | | 285 | | | | | | |
| CTG | GAC | ATG | TTG | GGG | GAC | GGG | GAT | TCC | CCG | GGT | CCG | GGA | TTT | ACC | CCC | 912 |
| Leu | Asp | Met | Leu | Gly | Asp | Gly | Asp | Ser | Pro | Gly | Pro | Gly | Phe | Thr | Pro | |
| | 290 | | | | | 295 | | | | | 300 | | | | | |
| CAC | GAC | TCC | GCC | CCC | TAC | GGC | GCT | CTG | GAT | ATG | GCC | GAC | TTC | GAG | TTT | 960 |
| His | Asp | Ser | Ala | Pro | Tyr | Gly | Ala | Leu | Asp | Met | Ala | Asp | Phe | Glu | Phe | |
| 305 | | | | | 310 | | | | | 315 | | | | | 320 | |
| GAG | CAG | ATG | TTT | ACC | GAT | CCC | CTT | GGA | ATT | GAC | GAG | TAC | GGT | GGG | TAG | 1008 |
| Glu | Gln | Met | Phe | Thr | Asp | Pro | Leu | Gly | Ile | Asp | Glu | Tyr | Gly | Gly | | |
| 325 | | | | | 330 | | | | | 335 | | | | | | |

( 2 ) INFORMATION FOR SEQ ID NO:2:

( i ) SEQUENCE CHARACTERISTICS:
        ( A ) LENGTH: 335 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ser | Arg | Leu | Asp | Lys | Ser | Lys | Val | Ile | Asn | Ser | Ala | Leu | Glu | Leu |
| 1 | | | | 5 | | | | | 10 | | | | | 15 | |
| Leu | Asn | Glu | Val | Gly | Ile | Glu | Gly | Leu | Thr | Thr | Arg | Lys | Leu | Ala | Gln |
| | 20 | | | | | 25 | | | | | 30 | | | | |
| Lys | Leu | Gly | Val | Glu | Gln | Pro | Thr | Leu | Tyr | Trp | His | Val | Lys | Asn | Lys |
| 35 | | | | | 40 | | | | | 45 | | | | | |
| Arg | Ala | Leu | Leu | Asp | Ala | Leu | Ala | Ile | Glu | Met | Leu | Asp | Arg | His | His |
| | 50 | | | | | 55 | | | | | 60 | | | | |
| Thr | His | Phe | Cys | Pro | Leu | Lys | Gly | Glu | Ser | Trp | Gln | Asp | Phe | Leu | Arg |
| 65 | | | | | 70 | | | | | 75 | | | | | 80 |
| Asn | Lys | Ala | Lys | Ser | Phe | Arg | Cys | Ala | Leu | Leu | Ser | His | Arg | Asn | Gly |
| 85 | | | | | 90 | | | | | 95 | | | | | |
| Ala | Lys | Val | His | Ser | Asp | Thr | Arg | Pro | Thr | Glu | Lys | Gln | Tyr | Glu | Thr |
| | 100 | | | | | 105 | | | | | 110 | | | | |
| Leu | Glu | Asn | Gln | Leu | Ala | Phe | Leu | Cys | Gln | Gln | Gly | Phe | Ser | Leu | Glu |
| 115 | | | | | 120 | | | | | 125 | | | | | |

| | | | | | | | | | | | | | |
|---|---|---|---|---|---|---|---|---|---|---|---|---|---|
| Asn | Ala | Leu | Tyr | Ala | Leu | Ser | Ala | Val | Gly | His | Phe | Thr | Leu | Gly | Cys |
| | 130 | | | | 135 | | | | | 140 | | | | |
| Val | Leu | Glu | Asp | Gln | Glu | His | Gln | Val | Ala | Lys | Glu | Glu | Arg | Glu | Thr |
| 145 | | | | | 150 | | | | | 155 | | | | | 160 |
| Pro | Thr | Thr | Asp | Ser | Met | Pro | Pro | Leu | Leu | Arg | Gln | Ala | Ile | Glu | Leu |
| 165 | | | | | 170 | | | | | 175 | | | | | |
| Phe | Asp | His | Gln | Gly | Ala | Glu | Pro | Ala | Phe | Leu | Phe | Gly | Leu | Glu | Leu |
| | 180 | | | | 185 | | | | | 190 | | | | | |
| Ile | Ile | Cys | Gly | Leu | Glu | Lys | Gln | Leu | Lys | Cys | Glu | Ser | Gly | Ser | Ala |
| 195 | | | | | 200 | | | | | 205 | | | | | |
| Tyr | Ser | Arg | Ala | Arg | Thr | Lys | Asn | Asn | Tyr | Gly | Ser | Thr | Ile | Glu | Gly |
| | 210 | | | | | 215 | | | | | 220 | | | | |
| Leu | Leu | Asp | Leu | Pro | Asp | Asp | Ala | Pro | Glu | Glu | Ala | Gly | Leu | Ala |
| 225 | | | | | 230 | | | | | 235 | | | | | 240 |
| Ala | Pro | Arg | Leu | Ser | Phe | Leu | Pro | Ala | Gly | His | Thr | Arg | Arg | Leu | Ser |
| 245 | | | | | 250 | | | | | 255 | | | | | |
| Thr | Ala | Pro | Pro | Thr | Asp | Val | Ser | Leu | Gly | Asp | Glu | Leu | His | Leu | Asp |
| 260 | | | | | 265 | | | | | 270 | | | | | |
| Gly | Glu | Asp | Val | Ala | Met | Ala | His | Ala | Asp | Ala | Leu | Asp | Asp | Phe | Asp |
| 275 | | | | | 280 | | | | | 285 | | | | | |
| Leu | Asp | Met | Leu | Gly | Asp | Gly | Asp | Ser | Pro | Gly | Pro | Gly | Phe | Thr | Pro |
| | 290 | | | | | 295 | | | | | 300 | | | | |
| His | Asp | Ser | Ala | Pro | Tyr | Gly | Ala | Leu | Asp | Met | Ala | Asp | Phe | Glu | Phe |
| 305 | | | | | 310 | | | | | 315 | | | | | 320 |
| Glu | Gln | Met | Phe | Thr | Asp | Pro | Leu | Gly | Ile | Asp | Glu | Tyr | Gly | Gly |
| 325 | | | | | 330 | | | | | 335 | | | | | |

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:3:

```
GAC  GCG  CTA  GAC  GAT  TTC  GAT  CTG  GAC  ATG  TTG           33
Asp  Ala  Leu  Asp  Asp  Phe  Asp  Leu  Asp  Met  Leu
 1              5                        10
```

(2) INFORMATION FOR SEQ ID NO:4:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:4:

```
Asp  Ala  Leu  Asp  Asp  Phe  Asp  Leu  Asp  Met  Leu
 1              5                        10
```

(2) INFORMATION FOR SEQ ID NO:5:

(i) SEQUENCE CHARACTERISTICS:
        (A) LENGTH: 7 amino acids
        (B) TYPE: amino acid
        (D) TOPOLOGY: linear 5,654,168

43 44

-continued ( i i ) MOLECULE TYPE: peptide ( v ) FRAGMENT TYPE: internal ( x i ) SEQUENCE DESCRIPTION: SEQ ID NO:5:

Met Pro Lys Arg Pro Arg Pro
1               5

( 2 ) INFORMATION FOR SEQ ID NO:6:

( i ) SEQUENCE CHARACTERISTICS:
        ( A ) LENGTH: 569 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:6:

| | | | | | |
|---|---|---|---|---|---|
| GAATTCGGGG | CCGCGGAGGC | TGGATCGGTC | CCGGTGTCTT | CTATGGAGGT | CAAAACAGCG | 60 |
| TGGATGGCGT | CTCCAGGCGA | TCTGACGGTT | CACTAAACGA | GCTCTGCTTA | TATAGGTCGA | 120 |
| GTTACCACT | CCCTATCAGT | GATAGAGAAA | AGTGAAAGTC | GAGTTACCA | CTCCCTATCA | 180 |
| GTGATAGAGA | AAAGTGAAAG | TCGAGTTTAC | CACTCCCTAT | CAGTGATAGA | GAAAAGTGAA | 240 |
| AGTCGAGTTT | ACCACTCCCT | ACCAGTGATA | GAGAAAGTG | AAAGTCGAGT | TTACCACTCC | 300 |
| CTATCAGTGA | TAGAGAAAAG | TGAAAGTCGA | GTTACCACT | CCCTATCAGT | GATAGAGAAA | 360 |
| AGTGAAAGTC | GAGTTTACCA | CTCCCTATCA | GTGATAGAGA | AAAGTGAAAG | TCGAGCTCGG | 420 |
| TACCCGGGTC | GAGTAGGCGT | GTACGGTGGG | AGGCCTATAT | AAGCAGAGCT | CGTTTAGTGA | 480 |
| ACCGTCAGAT | CGCCTGGAGA | CGCCATCCAC | GCTGTTTTGA | CCTCCATAGA | AGACACCGGG | 540 |
| ACCGATCCAG | CCTCCGCGGC | CCCGAATTC | | | | 569 |

( 2 ) INFORMATION FOR SEQ ID NO:7:

( i ) SEQUENCE CHARACTERISTICS:
        ( A ) LENGTH: 520 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:7:

| | | | | | |
|---|---|---|---|---|---|
| AGATCTGCAG | GGTCGCTCGG | TGTTCGAGGC | CACACGCGTC | ACCTTAATAT | GCGAAGTGGA | 60 |
| CCGGATCTCG | AGTTTACCAC | TCCCTATCAG | TGATAGAGAA | AAGTGAAAGT | CGAGTTTACC | 120 |
| ACTCCCTATC | AGTGATAGAG | AAAAGTGAAA | GTCGAGTTTA | CCACTCCCTA | TCAGTGATAG | 180 |
| AGAAAAGTGA | AAGTCGAGTT | TACCACTCCC | TATCAGTGAT | AGAGAAAAGT | GAAAGTCGAG | 240 |
| TTTACCACTC | CCTATCAGTG | ATAGAGAAAA | GTGAAAGTCG | AGTTACCAC | TCCCTATCAG | 300 |
| TGATAGAGAA | AAGTGAAAGT | CGAGTTTACC | ACTCCCTATC | AGTGATAGAG | AAAAGTGAAA | 360 |
| GTCGAGCTCG | GTACCCGGGT | CGAGTAGGCG | TGTACGGTGG | GAGGCCTATA | TAAGCAGAGC | 420 |
| TCGTTTAGTG | AACCGTCAGA | TCGCCTGGAG | ACGCCATCCA | CGCTGTTTTG | ACCTCCATAG | 480 |
| AAGACACCGG | GACCGATCCA | GCCTCCGCGG | CCCCGAATTC | | | 520 |

( 2 ) INFORMATION FOR SEQ ID NO:8:

( i ) SEQUENCE CHARACTERISTICS:
        ( A ) LENGTH: 450 base pairs
        ( B ) TYPE: nucleic acid ( C ) STRANDEDNESS: double
                        ( D ) TOPOLOGY: linear ( i i ) MOLECULE TYPE: DNA (genomic)

( v i ) ORIGINAL SOURCE:
                        ( A ) ORGANISM: Human cytomegalovirus
                        ( B ) STRAIN: K12, Towne ( i x ) FEATURE:
                        ( A ) NAME/KEY: mRNA
                        ( B ) LOCATION: 382..450

( x i ) SEQUENCE DESCRIPTION: SEQ ID NO:8:

| | | | | | | |
|---|---|---|---|---|---|---|
| GAATTCCTCG | AGTTTACCAC | TCCCTATCAG | TGATAGAGAA | AAGTGAAAGT | CGAGTTTACC | 60 |
| ACTCCCTATC | AGTGATAGAG | AAAAGTGAAA | GTCGAGTTTA | CCACTCCCTA | TCAGTGATAG | 120 |
| AGAAAAGTGA | AAGTCGAGTT | TACCACTCCC | TATCAGTGAT | AGAGAAAAGT | GAAAGTCGAG | 180 |
| TTTACCACTC | CCTATCAGTG | ATAGAGAAAA | GTGAAAGTCG | AGTTTACCAC | TCCCTATCAG | 240 |
| TGATAGAGAA | AAGTGAAAGT | CGAGTTTACC | ACTCCCTATC | AGTGATAGAG | AAAAGTGAAA | 300 |
| GTCGAGCTCG | GTACCCGGGT | CGAGTAGGCG | TGTACGGTGG | GAGGCCTATA | TAAGCAGAGC | 360 |
| TCGTTTAGTG | AACCGTCAGA | TCGCCTGGAG | ACGCCATCCA | CGCTGTTTTG | ACCTCCATAG | 420 |
| AAGACACCGG | GACCGATCCA | GCCTCCGCGG | | | | 450 |

( 2 ) INFORMATION FOR SEQ ID NO:9:

( i ) SEQUENCE CHARACTERISTICS:
                        ( A ) LENGTH: 450 base pairs
                        ( B ) TYPE: nucleic acid
                        ( C ) STRANDEDNESS: double
                        ( D ) TOPOLOGY: linear ( i i ) MOLECULE TYPE: DNA (genomic)

( v i ) ORIGINAL SOURCE:
                        ( A ) ORGANISM: Human cytomegalovirus
                        ( B ) STRAIN: Towne ( i x ) FEATURE:
                        ( A ) NAME/KEY: mRNA
                        ( B ) LOCATION: 382..450

( x i ) SEQUENCE DESCRIPTION: SEQ ID NO:9:

| | | | | | | |
|---|---|---|---|---|---|---|
| GAATTCCTCG | ACCCGGGTAC | CGAGCTCGAC | TTTCACTTTT | CTCTATCACT | GATAGGGAGT | 60 |
| GGTAAACTCG | ACTTTCACTT | TTCTCTATCA | CTGATAGGGA | GTGGTAAACT | CGACTTTCAC | 120 |
| TTTTCTCTAT | CACTGATAGG | GAGTGGTAAA | CTCGACTTTC | ACTTTTCTCT | ATCACTGATA | 180 |
| GGGAGTGGTA | AACTCGACTT | TCACTTTTCT | CTATCACTGA | TAGGGAGTGG | TAAACTCGAC | 240 |
| TTTCACTTTT | CTCTATCACT | GATAGGGAGT | GGTAAACTCG | ACTTTCACTT | TTCTCTATCA | 300 |
| CTGATAGGGA | GTGGTAAACT | CGAGTAGGCG | TGTACGGTGG | GAGGCCTATA | TAAGCAGAGC | 360 |
| TCGTTTAGTG | AACCGTCAGA | TCGCCTGGAG | ACGCCATCCA | CGCTGTTTTG | ACCTCCATAG | 420 |
| AAGACACCGG | GACCGATCCA | GCCTCCGCGG | | | | 450 |

( 2 ) INFORMATION FOR SEQ ID NO:10:

( i ) SEQUENCE CHARACTERISTICS:
                        ( A ) LENGTH: 398 base pairs
                        ( B ) TYPE: nucleic acid
                        ( C ) STRANDEDNESS: double
                        ( D ) TOPOLOGY: linear ( i i ) MOLECULE TYPE: DNA (genomic)

( v i ) ORIGINAL SOURCE:

(A) ORGANISM: Herpes Simplex Virus
(B) STRAIN: KOS (xi) SEQUENCE DESCRIPTION: SEQ ID NO:10:

```
GAGCTCGACT  TTCACTTTTC  TCTATCACTG  ATAGGGAGTG  GTAAACTCGA  CTTTCACTTT      60
TCTCTATCAC  TGATAGGGAG  TGGTAAACTC  GACTTTCACT  TTTCTCTATC  ACTGATAGGG     120
AGTGGTAAAC  TCGACTTTCA  CTTTTCTCTA  TCACTGATAG  GGAGTGGTAA  ACTCGACTTT    180
CACTTTTCTC  TATCACTGAT  AGGGAGTGGT  AAACTCGACT  TTCACTTTTC  TCTATCACTG    240
ATAGGGAGTG  GTAAACTCGA  CTTTCACTTT  TCTCTATCAC  TGATAGGGAG  TGGTAAACTC    300
GAGATCCGGC  GAATTCGAAC  ACGCAGATGC  AGTCGGGGCG  GCGCGGTCCG  AGGTCCACTT    360
CGCATATTAA  GGTGACGCGT  GTGGCCTCGA  ACACCGAG                              398
```

(2) INFORMATION FOR SEQ ID NO:11:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:11:

```
ACTTTATCAC  TGATAAACAA  ACTTATCAGT  GATAAAGA                               38
```

(2) INFORMATION FOR SEQ ID NO:12:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:12:

```
ACTCTATCAT  TGATAGAGTT  CCCTATCAGT  GATAGAGA                               38
```

(2) INFORMATION FOR SEQ ID NO:13:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:13:

```
AGCTTATCAT  CGATAAGCTA  GTTTATCACA  GTTAAATT                               38
```

(2) INFORMATION FOR SEQ ID NO:14:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:14:

```
ACTCTATCAT  TGATAGGGAA  CTCTATCAAT  GATAGGGA                               38
```

( 2 ) INFORMATION FOR SEQ ID NO:15:

( i ) SEQUENCE CHARACTERISTICS:
        ( A ) LENGTH: 38 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:15:

AATCTATCAC TGATAGAGTA CCCTATCATC GATAGAGA        38

We claim:

1. An isolated nucleic acid encoding a fusion protein which activates transcription, the fusion protein comprising a first polypeptide which binds to a tet operator sequence in the presence of tetracycline or a tetracycline analogue operatively linked to a second polypeptide which activates transcription in eukaryotic cells.

2. The nucleic acid of claim 1, wherein the first polypeptide is a mutated Tet repressor.

3. The nucleic acid of claim 2, wherein the mutated Tet repressor has at least one amino acid substitution compared to a wild-type Tet repressor.

4. The nucleic acid of claim 2, wherein the mutated Tet repressor has at least one amino acid addition or deletion compared to a wild-type Tet repressor.

5. The nucleic acid of claim 3, wherein the mutated Tet repressor is a mutated Tn10-derived Tet repressor having an amino acid substitution at at least one amino acid position selected from the group consisting of position 71, position 95, position 101 and position 102.

6. The nucleic acid of claim 5, wherein the mutated Tn10-derived Tet repressor comprises an amino acid sequence shown in positions 1 to 207 of SEQ ID NO: 2.

7. The nucleic acid of claim 1, wherein the second polypeptide comprises a transcription activation domain of herpes simplex virion protein 16.

8. The nucleic acid of claim 7, wherein the transcription activation domain comprises a C-terminal amino acid region of herpes simplex virus virion protein 16 comprising an amino acid sequence shown in positions 208 to 335 of SEQ ID NO: 2.

9. The nucleic acid of claim 7, wherein the transcription activation domain comprises at least one copy of a C-terminal region of herpes simplex virus virion protein 16 comprising an amino acid sequence shown in SEQ ID NO: 4.

10. The nucleic acid of claim 1, wherein the second polypeptide comprises a transcription activation domain selected from the group consisting of: an acidic transcription activation domain, a proline-rich transcription activation domain, a serine/threonine-rich transcription activation domain and a glutamine-rich transcription activation domain.

11. The nucleic acid molecule of claim 1, wherein the fusion protein further comprises an operatively linked third polypeptide which promotes transport of the fusion protein to a cell nucleus.

12. A recombinant vector comprising the nucleic acid molecule of claim 1 in a form suitable for expression of the fusion protein in a host cell.

13. The recombinant vector of claim 12, wherein expression of the fusion protein is regulated by at least one tissue-specific regulatory element.

14. The recombinant vector of claim 12 wherein expression of the fusion protein is regulated by at least one tet operator sequence.

15. A host cell comprising the recombinant vector of claim 12.

16. The host cell of claim 15, futher comprising a nucleotide sequence to be transcribed operatively linked to at least one tet operator sequence.

17. The host cell of claim 16, wherein the nucleotide sequence to be transcribed is an exogenous nucleotide sequence introduced into the host cell.

18. The host cell of claim 16, wherein the nucleotide sequence to be transcribed is an endogenous nucleotide sequence to which at least one tet operator sequence has been operatively linked.

19. The host cell of claim 16, which is a mammalian cell.

20. The host cell of claim 17, which is a human cell.

21. The host cell of claim 16, which is a yeast, insect or fungal cell.

22. A method for stimulating transcription of the nucleotide sequence operatively linked to the at least one tet operator sequence in the host cell of claim 16 comprising contacting the host cell with tetracycline or a tetracycline analogue.

23. The method of claim 22, wherein the tetracycline analogue is anhydrotetracycline or doxycycline.

24. A process for producing and isolating a protein comprising:
    a) growing the host cell of claim 16 at production scale in a culture medium in the presence of tetracycline or a tetracycline analogue to stimulate transcription of the nucleotides sequence operatively linked to the at least one tet operator sequence; and
    b) isolating a protein encoded by the nucleotide sequence from harvested host cells or from the culture medium.

25. The production process of claim 24, wherein the host cell is a mammalian, yeast or fungal cell.

26. A kit comprising a carrier means having in close confinement therein at least two container means comprising:
    a) a first container means containing a first nucleic acid encoding a fusion protein which activates transcription, the fusion protein comprising a polypeptide which binds to a first class of tet operator sequence in the presence of tetracycline or a tetracycline analogue operatively linked to a polypeptide which activates transcription in enkaryotic cells; and
    b) a second container means containing a second nucleic acid comprising a first cloning site for introduction of a first nucleotide sequence to be transcribed operatively linked to at least one tet operator sequence of a first class type.

27. The kit of claim 26, wherein the first container means contains a enkaryotic cell line into which the first nucleic acid has been stably introduced.

28. The kit of claim 26, further comprising a third container means containing a tetracycline or a tetracycline analogue.

29. The kit of claim 28, wherein the tetracycline analogue is anhydrotetracycline or doxycycline.

30. The kit of claim 26, wherein the second nucleic acid further comprises a second cloning site for introduction of a second nucleotide sequence of interest located at an opposite end of the at least one tet operator sequence relative to the first cloning site, wherein transcription of a first and second nucleotide sequence introduced into the second nucleic acid proceeds in opposite directions relative to the at least one tet operator sequence.

31. The kit of claim 26, further comprising:

c) a third container means containing a third nucleic acid encoding a second fusion protein which activates transcription, the second fusion protein comprising a polypeptide which binds to a tet operator sequence of a second class type in the absence of tetracycline or a tetracycline analogue operatively linked to a polypeptide which activates transcription in eukaryotic cells; and d) a fourth container means containing a fourth nucleic acid comprising a second cloning site for introduction of a second nucleotide sequence of interest operatively linked to at least one tet operator sequence of a second class type.

32. The kit of claim 31, further comprising a fifth container means containing a tetracycline or a tetracycline analogue.

33. The kit of claim 32, wherein the tetracycline analogue is anhydrotetracycline or doxycycline.

* * * * *